United States Patent
Veech

(10) Patent No.: US 6,323,237 B1
(45) Date of Patent: Nov. 27, 2001

(54) THERAPEUTIC COMPOSITIONS

(75) Inventor: Richard L. Veech, Rockville, MD (US)

(73) Assignee: BTG International Limited, London (GB)

( * ) Notice: Subject to any disclaimer, the term of this patent is extended or adjusted under 35 U.S.C. 154(b) by 0 days.

(21) Appl. No.: 09/397,100

(22) Filed: Sep. 16, 1999

Related U.S. Application Data

(63) Continuation-in-part of application No. PCT/US98/05072, filed on Mar. 17, 1998.
(60) Provisional application No. 60/040,858, filed on Mar. 17, 1997.

(51) Int. Cl.$^7$ ................................................. A61K 31/357
(52) U.S. Cl. ........................... 514/450; 514/546; 514/578
(58) Field of Search .................................... 514/546, 578, 514/450

(56) References Cited

U.S. PATENT DOCUMENTS

| | | |
|---|---|---|
| 4,067,999 | 1/1978 | Glabe et al. . |
| 4,234,599 | 11/1980 | Van Scott et al. . |
| 4,346,107 | 8/1982 | Cavazza et al. . |
| 4,351,835 | 9/1982 | Stanko . |
| 4,363,815 | 12/1982 | Yu et al. . |
| 4,579,955 | 4/1986 | Lammerant et al. . |
| 4,701,443 | 10/1987 | Nelson et al. . |
| 4,771,074 | 9/1988 | Lammerant et al. . |
| 4,929,449 | 5/1990 | Veech . |
| 4,970,143 | 11/1990 | Guidoux et al. . |
| 4,983,766 | 1/1991 | Imwinkelried et al. . |
| 4,997,976 | 3/1991 | Brunengraber et al. . |
| 5,100,677 | 3/1992 | Veech . |
| 5,116,868 | 5/1992 | Chen et al. . |
| 5,126,373 | 6/1992 | Bruengraber et al. . |
| 5,200,200 | 4/1993 | Veech . |
| 5,292,774 | 3/1994 | Hiraide et al. . |
| 5,348,979 | 9/1994 | Nissen et al. . |
| 5,654,266 | 8/1997 | Chen et al. . |
| 5,693,850 | 12/1997 | Birkhahn et al. . |
| 5,719,119 | 2/1998 | Veech . |
| 5,912,269 | 1/1999 | Tung . |

FOREIGN PATENT DOCUMENTS

| | | |
|---|---|---|
| 0108820 | 11/1982 | (EP) . |
| 0288908 | 4/1988 | (EP) . |
| 0318357 | 11/1988 | (EP) . |
| 0466050 | 7/1991 | (EP) . |
| 0562188 | 3/1992 | (EP) . |
| 0552896 | 1/1993 | (EP) . |
| 0780123 | 11/1996 | (EP) . |
| 2126082 | 8/1992 | (GB) . |
| WO 92/09210 | 11/1991 | (WO) . |
| WO 92/09211 | 11/1991 | (WO) . |
| WO 98/41201 | 3/1998 | (WO) . |
| WO 98/51812 | 5/1998 | (WO) . |
| WO 99/34687 | 1/1999 | (WO) . |

OTHER PUBLICATIONS

"Biopolymers and –oligomers of (R)–3–Hydroxyalkanoic Acids—Contributions of synthetic Organic Chemists"; D Seebach et al; Ernst Schering Research Foundation; 1995.

"Biodegradation of cyclic and substituted linear oligomers of poly(3–hydroxybutyrate)"; Helmut Brandl et al; Can. J. Microbiol 41 (Suppl. 1); 1995; pp. 180–186.

"Direct degradation of the biopolymer poly [(R)–3–hydroxybutyric acid] to (R)–3 hydroxybutanoic acid and its methyl ester"; D Seebach et al; Org. Synth. 71; 1992; pp. 39–47.

"Cyclische Oligomere von (R)–3–Hydroxybuttersäure: Herstellung und strukturelle Aspekte"; von Dietmar et al; Helvetica Chimica Acta; vol. 76; 1993; pp. 2004–2016.

"Poly(hydroxyalkaloates): A Fifth Class of Physiologically Important Organic Biopolymers?"; Hans–Martin Müller et al; Angew. Chem.; 1993.

"Intractable epilepsy"; Avinoam Scuper et al; The Lancet, vol. 353; Apr. 10, 1999; p. 1238.

"Energy Metabolism and the Regulation of Metabolic Processes in Mitochondria"; R L Veech et al; Academic Press; 1972; pp. 170–183.

"Nontoxic Amyloid β Peptide$_{1-42}$ suppresses Acetylcholine synthesis"; Minako Hoshi et al; The Journal of Biological Chemistry; vol. 272, No. 4; Jan. 1997; pp. 2038–2041.

"Alternate Fuel Utilization by Brain"; George F Cahill Jr et al; Cerebral Metabolism and Neural Function; Williams & Wilkins, London; pp. 234–242.

"Preparation and Structure of Oligolides from (R)–3–Hydroxypentanoic Acid and comparison with the Hydroxybutanoic–Acid Derivatives: A Small Change with Large Consequences"; Dieter Seebach et al; Helvetica Chimica Acta—vol. 77; 1994; pp. 2007–2033.

(List continued on next page.)

*Primary Examiner*—James H. Reamer
(74) *Attorney, Agent, or Firm*—Nixon & Vanderhye

(57) ABSTRACT

Compositions comprising ketone bodies and/or their metabolic precursors are provided that are suitable for administration to humans and animals and which have the properties of, inter alia, (i) increasing cardiac efficiency, particularly efficiency in use of glucose, (ii) for providing energy source, particularly in diabetes and insulin resistant states and (iii) treating disorders caused by damage to brain cells, particularly by retarding or preventing brain damage in memory associated brain areas such as found in Alzheimer's and similar conditions.

These compositions may be taken as nutritional aids, for example for athletes, or for the treatment of medical conditions, particularly those associated with poor cardiac efficiency, insulin resistance and neuronal damage. The invention further provides methods of treatment and novel esters and polymers for inclusion in the compositions of the invention.

19 Claims, 2 Drawing Sheets

OTHER PUBLICATIONS

"The Triolide of (R)–3–Hydroxybutyric acid—Direct Preparation from Polyhydroxybutrate and Formation of a Crown Estercarbonly Complex with Na Ions"; Dieter Seebach et al; Angew. Chem. Int.; 1992; pp. 434–435.

"Ketone bodies as substrates"; A J Rich; Proceedings of the Nutrition Society, vol. 49, 1990; pp. 361–373.

"The Dimer and Trimer of 3–Hydroxybutyrate Oligomer as a Precursor of Ketone Bodies for Nutritional Care"; Osamu Tasaki et al; Journal of Parenteral and Enteral Nutrition, vol. 23, No. 6; 1999; pp. 321–325.

"Effect of 3–hydroxybutyrate in obese subjects on very–low–energy diets and during therapeutic starvation"; G L S Pawan et al; The Lancet; Jan. 1983; pp. 15–17.

"The untoward effects of the anoins of dialysis fluids"; R L Veech et al; Kidney Internation, vol. 34; 1988; pp. 587–597.

"Transport of poly–β–hydroxybutyrate in human plasma"; Rosetta N. Reusch et al; Biochimica et Biophysica Acta 1123; 1192; pp. 33–40.

"Human xenobiotic metabolizing esterases in liver and blood"; N W McCraken et al; Biochemical Pharmacology vol. 46, No. 7; 1993; pp. 1125–1129.

"Detection, synthesis, structure, and function of oligo(3–hydroxyalkanoates); contributions by synthetic organic chemists"; Dieter Seebach et al; International Journal of Biological Macromolecules 25; 1999; pp. 217–236.

"Poly(hydroxyalkanoates): A Fifth Class of Physiologically Important Organic Biopolymers?" Hans–Martin Müller et al; Angewandte Chemie vol. 32, No. 4; Apr. 1993; pp. 477–502.

"The toxic impact of parenteral solutions on the metabolism of cells; a hypothesis for physiological parenteral therapy"; R L Veech et al; The Americal Journal of Clinical Nutrition 44: Oct. 1986; pp. 519–551.

"Association between features of the insulin resistance syndrome and Alzheimer's disease independently of apolipoprotein E4 phenotype: cross sectional population based study"; Johanna Kuusisto et al; BMJ vol. 315; Oct. 25, 1997; pp. 1045–1049.

"Novel calcium ion channel is a pore without protein"; Karen Hopkin; The Journal of NIH Research vol. 9; Nov. 1997; pp. 25–26.

"Physiological Roles of Ketone Bodies as Substrates and Signals in Mammalian Tissues"; Alison M Robinson et al; Physiological Reviews vol. 60, No. 1; Jan. 1980; pp. 143–153.

"Proof for a nonproteinaceous calcium–selective channel in *Escherichia coli* by total synthesis from (R)–3–hydroxybutanoic acid and inorganic polyphosphate"; Sudipto Das et al; Proc. Natl. Acad. Sci. USA vol. 94; Aug. 1997; pp. 9075–9079.

"New clues to Alzheimer's disease: Unraveling the roles of amyloid and tau"; Bruce A Yankner; Nature Medicine vol. 2, No. 8; Aug. 1996; pp. 850–852.

"An intracellular protein that binds amyloid–β peptide and mediates neurotoxicity in Alzheimer's disease"; Shi Du Yan et al; Nature, vol. 389; Oct. 16, 1997; pp. 689–695.

"Alternate Fuel Utilization by Brain"; George F Cahill, Jr et al; Cerebral Metabolism and Neural Function; Williams & Wilkins; Chapter 26, pp. 234–242.

"Blood–Brain Barrier Transport of Metabolic Substrates"; William H Oldendorf; Cerebral Metabolism and Neural Function; Williams & Wilkins; Chapter 15, pp. 127–132.

"β–hydroxybutyrate suppresses pentylenetetrazol (PTZ)—induced seizures in young adult rats"; Sarah Lustig et al; Epilepsia, vol. 39, Suppl. 6; 1998; 2.020; p. 36.

"β–hydroxybutyrate potentiates $gaba_A$–mediated inhibitory postsynaptic potentials in immature hippocampal CA1 neurons"; Shundi Ge et al; Epilepsia, vol. 39, Suppl. 6; 1998; E.06; p. 135.

"The effect of ketone bodies, β–hydroxybutyrate, and acetoacetate on acute seizure activity in hippocampal CA1 neurons"; Charles E. Neisen et al; Epilepsia, vol. 39, Suppl. 6; 1998; 2.015; p. 35.

"Biologica–Chemical preparation of 3–hydroxycarboxylic acids and their use in EPC–syntheses"; Dieter Seebach et al; Laboratorium für Organische Chemie der Eidgenössischen Technischen Hochschule; pp. 85–126.

"Dietary Nonprotein calories and cerebral infarction size in rats"; Claudia Robertson et al; Stroke, vol. 23, No. 4; Apr. 1992; pp. 564–568.

"Hypoxia and β–hydroxybutyrate acutely reduce glucose extraction by the brain in anesthetized dogs"; Albert S Y Change et al; Can J Phyiol Pharmacol, vol. 71; 1993; pp. 465–472.

"γ–Hydroxybutyrate: Cerebral metabolic, Vascular, and Protective effects"; Alan A Artre et al; J Neurochem, vol. 35, No. 5; 1980; pp. 1114–1119.

"Effect of sodium hydroxybutyrate on the cerebral circulation and regional vasomotor reflexes"; E A Bendikov et al; Plenum Publishing Corporation; 1980; pp. 1287–1292.

"Oxidative metabolism deficiencies in brains of patients with Alzheimer's disease"; S Hoyer, Acta Neurol Scand, Suppl. 165; 1996; pp. 18–24.

"The ins and outs of amyloid–β"; Konrad Beyreuther et al; Nature, vol. 389; Oct. 16, 1997; pp. 677–678.

"Metabolism of (R,S)–1,3–butanediol acetoacetate esters, potential parenteral and enteral nutrients in conscious pigs"; Sylvain Desrochers et al; The American Physiological Society; 1995; pp. 660–667.

"The Gibbs–Donnan Near–equilibrium System of Heart"; Takashi Masuda et al; The Journal of Biological Chemistry, vol. 265, No. 33; Nov. 25, 1990; pp. 20321–20334.

"Nutritional and metabolic studies in humans with 1,3–butanediol"; Richard B Tobin et al; Federation Proceedings vol. 34, No. 12; Nov. 1975; pp. 2171–2176.

"Utilization of 1,3–Butanediol and Nonspecific Nitrogen in Human Adults"; Constance Kies et al; Nebraska Agriculture Research Station Journal No. 3489; pp. 1155–1163.

"Alzheimer's Disease: Genotypes, Phenotype, and Treatments"; Dennis J Selkoe; Science, vol. 275; Jan. 31, 1997; pp. 630–631.

"The β/α Peak Height Ration of ATP"; Kieran Clarke et al; The Journal of Biological Chemistry, vol. 271, No. 35, Aug. 30, 1996; pp. 21141–21150.

"Control of Glucose Utilization in Working Perfused Rat Heart"; Yoshishiro Kashiwaya et al; The Jourrnal of Biological Chemistry, vol. 269, No. 41; Oct. 14, 1994; pp. 25502–25514.

"Regulation of mitochondrial pyruvate dehydrogenase activity by tau protein kinase I/glycogen synthase kinase 3β in brain"; Minako Hoshi et al; Proc Natl. Acad. Sci. USA, vol. 93; Apr. 1996; pp. 2719–2723.

Stress and Glucocorticoid; Rachel Yehuda; Science, vol. 275; Mar. 14, 1997; pp. 1662–1663.

"Nontoxic Amyloid β Peptide$_{1-42}$ Suppresses acetylcholine synthesis"; Minako Hoshi et al; The Journal of Biological Chemistry, vol. 272, No. 4; Jan. 24, 1997; pp. 2038–2041.

"Metabolic engineering and human disease"; Martin L Yarmush et al; Nature Biotechnology, vol. 15; Jun. 15, 1997; pp. 525–528.

"Metabolism of R– and S–1,3–butanediol in perfused livers from meal–fed and starved rats"; Sylvain Desrochers et al; Biochem. J, vol. 285; 1992, pp. 647–653.

"Metabolism of 2,3–Butanediol Steroisomers in the Perfused Rat Liver"; Jan A Montgomery et al; The Journal of Biological Chemistry, vol. 268, No. 27; 1993; pp. 20185–20190.

"Nutritional and metabolic studies in humans with 1,3–butanediol"; Richard B Tobin et al; Federation Proceedings vol. 34, No. 12; Nov. 1975; pp. 2171–2176.

"Metabolic effects of a D–β–hydroxybutyrate infusion in septic patients: Inhibition of lipolysis and glucose production but not leucine oxidation"; Michel Beylot et al; Critical Care Medicine, vol. 22, No. 7; Jul. 1994; pp. 1091–1098.

"Hyperinsulinaemia and Alzheimer's Disease"; George Razay et al; Age and Ageing; 1994; pp. 398–399.

"Peripheral glucose metabolism and insulin sensitivity in Alzheimer's disease"; Kilander et al; Acta Neurol Scand; 1993; pp. 294–298.

"Effect of Sodium Hydroxybutyrate of the cerebral circulation and regional vasomotor reflexes"; Bendikov et al; Byulleten' Eksperimental'noi Biologii i Meditsiny, vol. 88 No. 11; Nov. 1979; pp. 555–557.

"Tau protein Mutations confirmed as neuron killers"; Gretchen Vogel; Science, vol. 280; Jun. 5, 1998; pp. 1524–1525.

"Diagnosing dementia with Lewy bodies"; Ian G McKeith et al; The Lancet, vol. 354; Oct. 9, 1999; pp. 1227–1228.

"R,S–1,3–butanediol acetoacetate esters, potential alternates to lipid emulsions for total parenteral nutrition"; Sylvain Desrochers et al; Nutritional Biochemistry vol. 6; 1995; pp. 111–118.

"Substrate signaling by insulin: a ketone bodies ration mimics insulin action in heart"; Yoshihiro Kashiwaya et al; The American Journal of Carliology, vol. 80 (3A); Aug. 4 1997; pp. 50–64.

"Insulin, ketone bodies, and mitochondrial energy transduction"; Kiyotaka Sato et al; The FASEB Journal, vol. 9; May 1995; pp. 651–658.

"Regulation of GABA Level in Rat Brain Synaptosomes: Fluxes through enzymes of the GABA shunt and effects of glutamate, calcium, and ketone bodies"; Maria Erecińska et al; Journal of Neurochemistry, vol. 67, No. 6; 1996; pp. 2325–2334.

"The Metabolism of Acetone in Rat"; Joseph P Cassazza et al; The Journal of Biological Chemistry, vol. 259, No. 1; Jan. 10, 1984; pp. 231–236.

THERAPEUTIC COMPOSITIONS

This is a continuation in part of PCT application No. PCT/US98/05072, filed Mar. 17, 1997; the entire content of which is hereby incorporated by reference in this application.

This application claims the benefit of U.S. Provisional Application No. 60/040,858, filed Mar. 17, 1997, the entire content of which is hereby incorporated by reference in this application.

The present invention relates to compositions suitable for administration to humans and animals which have the properties of, inter alia, (i) increasing cardiac efficiency, particularly efficiency in use of glucose, (ii) for providing energy source, particularly in diabetes and insulin resistant states and (iii) treating disorders caused by damage to brain cells, particularly by retarding or preventing brain damage in memory associated brain areas such as found in Alzheimer's and similar conditions. These compositions may be taken as nutritional aids, for example for athletes, or for the treatment of medical conditions, particularly those associated with poor cardiac efficiency, insulin resistance and memory loss. The invention further provides methods of treatment and novel esters and polymers for inclusion in the compositions of the invention.

Abnormal elevation of blood sugar occurs not only in insulin deficient and non insulin dependent diabetes but also in a variety of other diseases. The hyperglycaemia of diabetes results from an inability to metabolize and the over production of glucose. Both types of diabetes are treated with diet; Type I diabetes almost always requires additional insulin, whereas non-insulin dependent diabetes, such as senile onset diabetes, may be treated with diet and weight loss, although insulin is increasingly used to control hyperglycaemia.

Increased sympathetic stimulation or elevated glucagon levels, in addition to increasing glycogenolysis in liver, also stimulate free fatty acid release from adipocytes. After acute myocardial infarction or during heart failure, increased sympathetic nervous activity or administration of sympathornimetics accelerate glycogenolysis, decrease release of insulin from P cells of the pancreas and cause relative insulin resistance. While the importance of diet, or substrate availability, is taken as a given in the treatment of diabetes, the critical effects of substrate choice in insulin resistant states has not been widely appreciated or applied in clinical practice. Instead contemporary interest has focused upon the complex signalling cascade which follows the binding of insulin to its receptor. This increasingly complex cascade of messages involving protein tyrosine kinases and phosphatases, inositol and other phospholipids, while holding promise for the ultimate understanding of non-insulin dependent diabetes, has yet to provide significant new therapies for either diabetes or insulin resistance.

Leaving aside the longer term effects of insulin on growth, the acute metabolic effects of insulin have been thought to be accounted for by action at three major enzymatic steps in the conversion of glucose to $CO_2$. Firstly insulin promotes the translocation of the glucose transporter, Glut4, from endoplasmic reticular to plasma membranes, thus increasing the transport of glucose from the extra to intracellular phase.(see refs. 1 and 2). Secondly, insulin increases the accumulation of glycogen. This has been attributed to dephosphorylation of glycogen synthase (3) by protein phosphatase 1. Thirdly, insulin stimulates the activity of mitochondrial pyruvate dehydrogenase multi-enzyme complex (4 and 5) through dephosphorylation by a $Ca^{2+}$ sensitive (6) intramitochondrial protein phosphatase.

An important, but poorly understood effect of insulin is its use in cardiac disease where in combination with glucose, potassium chloride and GIK, it improved electrocardiographic abnormalities accompanying myocardial infarction (7 and 8), and improved cardiac performance after post pump stunning (9). This treatment has been advocated recently for a number of other serious cardiac diseases (10 and 11). The beneficial effects of GIK infusion have been attributed to its ability to decrease free fatty acid release and improve membrane stability (12). However, other more recent work suggests more fundamental reasons. In heart cells that are anoxic, glucose is the only fuel capable of providing the ATP necessary to maintain viability (13).

Administration of glucose plus insulin would increase the availability of intracellular glucose providing a source of ATP production in the absence of $O_2$. While this would explain certain beneficial effects, it would not account for the correction of EKG abnormalities nor the improved cardiac index in hearts treated with GIK because electrical activity and cardiac work requires actively respiring cardiac cells, not ones which are totally anoxic and therefore without electrical activity or the ability to perform mechanical work.

Understanding the enzymatic sites of insulin's action does not, by itself, define the effects of insulin deficiency upon the cellular metabolism or physiological function. How insulin acts at this larger level can best be understood by looking at the way nature deals with insulin deficiency. The natural compensation for decreased insulin during fasting is the accelerated hepatic conversion of the free fatty acids to the ketone bodies raising blood D-β-hydroxybutyrate and acetoacetate to about 6 mM. At these levels, ketones, rather than glucose, become the substrate for most organs, including even the brain (14). Although mild ketosis is the normal response to decreased insulin, physicians fear ketone bodies because their massive overproduction can be life threatening in diabetic ketoacidosis.

The present inventor has previously compared the effect of physiological levels of ketone bodies to the metabolic and physiological effects of insulin, particularly comparing the insulin deficient working rat heart perfused with glucose alone, to hearts to which was added either 4 mM D-β-hydroxybutyrate/1 mM acetoacetate, saturating doses of insulin or the combination and has shown how provision of simple substrates can mimic the effects of insulin in changing the concentrations of the intermediates of both glycolysis and the TCA cycle and thereby controlling the flux of glucose in this very specialised tissue. In addition he has determined that a primary but previously unrecognized effect of insulin or a ratio of ketones is to alter mitochondrial redox states in such a way so as to increase the $\Delta GA_{ATPhydrlysis}$ and with that, the gradients of inorganic ions between the various cellular phases and the physiological performance of heart.

The present application teaches that such ketone bodies can also provide a therapeutic approach to the treatment of insulin resistance where the normal insulin signalling pathway is disordered and in conditions where the efficiency of cardiac hydraulic work is decreased for metabolic reasons. The inventor has determined that use of ketone bodies has great advantage over use of insulin itself for reasons that will become evident from the description below, not least of these being the elimination of carbohydrate intake control otherwise necessary.

The present application further addresses the problem of neurodegenerative diseases, particularly disease where neurons are subject to neurotoxic effects of pathogenic agents such as protein plaques and further provides compositions for use in treating these and the aforesaid disorders.

Alzheimer's disease is a genetically heterogeneous group of progressively fatal neurological diseases characterized pathologically by accumulation of amyloid plaques in brain and clinically by impairment of recent memory leading to dementia and death. In addition to the cases of Alzheimer's disease linked to genetic causes, sporadic cases, without an apparent family history of the disease, also occur. For example pathological changes characteristic of Alzheimer's disease occur after head trauma (73) or after inflammatory diseases stimulating production of the cytokine interleukin-1 (97).

The early symptom of the disease is loss of recent memory associated with impairment and death of cell in the hippocampus accounting for the early impairment of recent memory. Measurement of the hippocampal volumes using magnetic resonance imaging (MRI) shows that atrophy of hippocampus occurs prior to the clinical onset of memory loss and progresses with a loss of volume of about 8% per year during the 2 years over which symptoms first appeared (70).

The diagnosis of Alzheimer's disease is made clinically by this impairment in recent memory, associated with lesions in the hippocampal portion of the temporal lobe. Neuropathologically, the diagnosis depends upon the finding of neurofibrillatory tangles within the cells, amyloid or senile plaques in the extracellular space and loss of neuronal number (61). The neurofibrillatory tangles are comprised of paired hyperphosphorylated tau protein, whose usual function in the cell, when not phosphorylated, is to bind to and stabilize tubulin in its formation of microtubules within the cell. Hyperphosphorylation of tau is catalysed by glycogen synthase kinase 3β, among other kinases and dephosphorylated by protein phosphatase 2A-1, 2B or 1(108).

However, there is not necessarily a clear, bright line between the pathological brain changes and the memory deficits which occur prematurely in Alzheimer's disease and the pathological changes in brain anatomy and memory function which are found in the "normal" aging population. Rather the difference is a quantitative one dependent upon rate (94). Such changes in memory function in the normal aged are also accompanied by a decreased glucose tolerance signifying an inability to metabolize glucose. In such situations, treatments aimed at rectifying the pathophysiological processes of Alzheimer's disease, would be expected to be applicable to the correction of the metabolic effects associated with normal aging.

While Alzheimer's disease of the familial or the sporadic type is the major dementia found in the aging population, other types of dementia are also found. These include but are not limited to: the fronto-temporal degeneration associated with Pick's disease, vascular dementia, senile dementia of Lewy body type, dementia of Parkinsonism with frontal atrophy, progressive supranuclear palsy and corticobasal degeneration and Downs syndrome associated Alzheimers'. Plaque formation is also seen in the spongiform encephalopathies such as CJD, scrapie and BSE. The present invention is directed to treatment of such neurodegenerative diseases, particularly those involving neurotoxic protein plaques, eg. amyloid plaques.

Many of these aforesaid apparently unrelated conditions have the hyperphosphorylated tau proteins found in Alzheimer's disease (69), opening up the possibility that the same kinase which phosphorylated tau would also phosphorylate the PDH complex producing a similar deficiency in mitochondrial energy production and acetyl choline synthesis found in Alzheimer's disease but involving other brain regions. The present inventor has determined that in this respect treatments applicable to Alzheimer's disease might be applied to these diseases as well. In addition, the inventor has determined that such treatment will also be applicable to peripheral neurological wasting diseases, such as myasthenia gravis and muscular dystrophy.

At present there is no effective treatment for Alheimer's disease. Research efforts are focused on defining its genetic cause but to date there has been no succesful gene therapy. Genetic studies have linked Alzeimer's disease with Mongolism and in its early onset form to locus on chromosome 21 causing accumulation of amyloid precursor protein (APP)(73), a transmembrane glycoprotein existing in 8 isoforms. Numerous fragments of this protein are derived by proteolysis and the plaques characteristic of Alzheimer's disease have been shown to contain accumulation of the oligomer of β amyloid protein (A $β_{1-42}$) An early onset autosomally dominant form of Alzheimer's disease has also been related to a presenilin 1 locus on chromosome 14.

A late onset form of Alzheimer's disease is associated with the type 4 allele of apolipoprotein E (69,98) on chromosome 19, although other workers suggest that this apparent correlation may be related instead of α 1 antichymotrypsin locus instead (100). All transgenic mice expressing increased amounts of amyloid precursor protein over 18 months of age showed hippocampal degeneration with many of the pathological characteristics of Alzheimer's disease (90).

The current status of knowledge on the defective genes and gene products in Alzheimer's disease has recently been summarized (Table 1 of ref. 96).

| Chromosome | Gene Defect | Age of Onset | Aβ Phenotype |
|---|---|---|---|
| 21 | βAPP mutations | 50's | Production of total Aβ peptides of A$β_{1-42}$ |
| 19 | apoE4 polymorphism | 60's or > | density of Aβ plaques and vascular deposits |
| 14 | Presenilin 1 mutations | 40's & 50's | production of A$β_{1-42}$ |
| 1 | Presenilin 2 mutations | 50's | production of A$β_{1-42}$ |

It is clear from the above table that the common phenotype associated with the genetic forms of Alzheimer's disease is the accumulation of the amyloid peptide A$β_{1-42}$ (96). It is this A$β_{1-42}$ which inactivates PDH thus impairing mitochondrial energy and citrate production in normally obligate glucose consuming tissue (95) and at the same time impairing synthesis of the critical neurotransmitter, acetyl choline (67,68). The application of A$β_{1-42}$ to neuronal cells is associated with the downregulation of the anti-apototic protein bcl-1 and increases levels of bax, a protein known to be associated with cell death (92). In addition to amyloid plaques comprised of A$β_{1-42}$ neurofibrillatory tangles comprised of hyperphosphorylated tau protein, and decreased brain acetyl choline levels, cell death is the fourth pathological characteristic of Alzheimer's disease. These pathological characteristics can be related, at least in part, to excess A$β_{1-42}$ and its inhibition of PDH.

Modest clinical improvement in symptoms can occur by treatment with acetyl choline esterase inhibitors (57), presumably by increasing cholinergic efferents originating in the septal nuclei and traversing Broca's diagonal band to hippocampus in the anterior portion of the limbic system of brain. However the progress in the molecular biology of Alzheimer's disease has caused the search for new therapies to concentrate upon four major areas (96): (i) protease inhibitors that partially decrease the activity of the enzymes (β and γ secretase) that cleave Aβ (β amyloid fragments) from βAPP (β amyloid precursor proteins); (ii) compounds that bind to extracellular Aβ that prevent its cytotoxic effects; (iii) brain specific anti-inflammatory drugs that block the microglial (brain macrophages) activation, cytokine release, and acute phase response that occur in affected brain regions; and (iv) compounds such as antioxidants, neuronal calcium channel blocks, or antiapoptotic agents that interfere with the mechanisms of Aβ triggered neurotoxicity.

The therapy which the present inventor now proposes differs from the four approaches listed above in that it bypasses the block in metabolic energy production resulting from inhibition of PDH by $A\beta_{1-42}$ by administering ketone bodies or their precursors. Neuronal cells are capable of metabolizing such compounds even in the presence of a deficiency of glucose, the normal energy substrate for brain (63). Because ketones can increase the ΔG of ATP hydrolysis, the gradients of both intracellular $Na^+$ and $Ca^{2+}$ will be increased, preventing cell death associated with increased intracellular Ca2+. Furthermore, the increase in citrate generation by the Krebs cycle will provide, when translocated into cytoplasm, a source of cytoplasmic acetyl CoA required to remedy the deficiency of acetyl choline characteristic of Alzheimer's brains.

The elevation of blood ketones necessary to correct these metabolic defects can be accomplished by parenteral, enteral means or dietary means and does not require the administration of potentially toxic pharmacological agents.

There has been long experience with ketogenic diets in children treated for epilepsy. Such diets are however unsuitable for use in adults due to adverse efects on the circulatory system. The present inventions application of ketone bodies should provide all the therapeutic effects of such diet, which is not itself found to be toxic in children, with none of the side effects that render it unused adults. Furthermore, the inventor has determined that with the correction of the aforesaid metabolic defects, cytokine responses and the increase in apoptotic peptides in degenerating cells will decrease due to the increase in neuronal cell energy status and the increased trophic stimulation resulting from increased acetyl choline synthesis.

Since the priority date of this application, EP 0780123 A1 has been published which relates to use of acetoacetate, β-hydroxybutyrate, monhydric, dihydric or trihydric alcohol esters of these or oligomers of β-hydroxybutyrate for suppressing cerebral edema, protecting cerebral function, rectifying cerebral energy metabolism and reducing the extent of cerebral infarction. It should be noted however, that it has been known since 1979 that sodium hydroxybutyrate increases cerebral circulation and regional vasomotor reflexes by up to 40% (Biull.Eksp.Biol.Med Vol 88 11, pp 555–557). The treatment that the present inventor now provides goes beyond such effects on circulation as it provides treatment for cells that are unable to function due to neurodegeneration, eg caused by neurotoxic agents such as peptides and proteins, and genetic abnormality. The treatment involves action of ketone bodies on the cells themselves and not the flow of blood to them.

In reducing this invention to practice the inventor has further determined that ketone bodies, provided by direct adminsitration or by administration of their metabolic precursors in amounts sufficient to raise total blood ketone body concentration to elevated levels result in more than simple maintenance of cell viability but actually improve cell function and growth beyond that of normal, ie. control levels in a manner unrelated to blood flow or nutrition. In this respect the invention further provides use of ketone bodies as nerve stimulant factors, ie. nerve growth factors and factors capable of stimulating enhanced neuronal function, such as increase of metabolic rate and.increase of extent of functional features such as axons and dendrites. This aspect of the present invention offers a mechanism for improvement of neuronal function as well as mere retardation of degredation.

The recent work of Hoshi and collaborators (77, 78) strongly suggests that a part of the amyloid protein whose accumulation is the hallmark of Alheimer's disease, $A\beta_{1-42}$, acts as a mitochondrial histidine protein kinase which phosphorylates and inactivates the pyruvate dehydrogenase multienzyme complex. The PDH complex is a mitochondrial enzyme responsible for the generation of acetyl CoA and NADH from the pyruvate produced by glycolysis within the cytoplasm. The mitochondrial acetyl CoA formed condenses with oxaloacetate to start the Krebs TCA cycle completely combusting pyruvate to $CO_2$ while providing the mitochondria with the reducing power which becomes the substrate for the electron transport system through which the energy required for mitochondrial ATP synthesis is generated. PDH thus stands at the crossroads of the two major energy producing pathways of the cell, glycolysis and the Krebs cycle, and clearly serves a critical function in living cells.

There are two major consequences of the inhibition of PDH. Firstly, in neuronal tissues, which under normal metabolic conditions are totally dependent upon glucose for energy production, inhibition of PDH results in a lowered efficiency of energy production, a lowered energy of hydrolysis of ATP, a decrease in both acetyl CoA and the metabolites of the first ⅓ of the TCA cycle and a deficiency of mitochondrial NADH (95). A decrease in the energy of ATP hydrolysis leads to increased intracellular $Na^+$ and $Ca^{2+}$, loss of cellular $K^+$ and ultimately cell death (86). Hippocampal cells, critical for the fixation of recent memories, are particularly sensitive to a number of forms of injury, and the death of these cells is the hallmark both clinically and pathologically of Alzheimer's disease.

A second major consequence of PDH inhibition is a deficiency of mitochondrial citrate (95). Citrate, or one of its metabolites, is exported to the cytoplasm from mitochondria where it is converted to cytosolic acetyl CoA by ATP citrate lyase (EC 4.1.3.8) in the reaction:

$$citrate^{3-}+ATP^{4-}+CoASH>acetyl\ CoA+oxaloacetate^{2-}+ADP^{3-}+HPO_4^{2-}$$

The acetyl CoA then combines with choline through the action of choline acetyl transferase (EC 2.3.1.6) to form acetyl choline in the reaction:

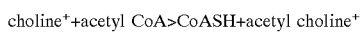

$$choline^+ + acetyl\ CoA > CoASH + acetyl\ choline^+$$

Neuronal culture of septal cells exposed to 1 μm $A\beta_{1-42}$ for 24 hours showed a decrease in acetyl choline production of over five fold (78) with no decrease in the activity of choline acetyl transferase. The inferred cause of this decreased production was a deficiency of acetyl CoA due to inhibition of the PDH complex caused by activation of the TPKI/GSK-3β protein kinase and subsequent phosphorylation of PDH (77).

As explained above isolated working hearts perfused with 10 mM glucose alone without insulin are inefficient and have impaired mitochondrial energy production. This defect in cellular energy production can be completely reversed by the provision of a physiological ratio of ketone bodies consisting of 4 mM D-β hydroxybutyrate and 1 mM acetoacetate (95). Brain was thought to be capable of using only glucose as its metabolic energy source and to be insensitive to the actions of insulin. However, in a remarkable clinical study performed in 1967, George Cahill and his collaborators (47) showed that up to 60% of the brain's need for metabolic energy could be met by ketone bodies in obese patients undergoing prolonged fasting. Even more remarkably, Cahill showed that administration of insulin to these patients in doses sufficient to drop their blood sugar from 4 to under 2 mM was associated with no impairment of mental functions in these patients whose blood D-β hydroxybutyrate was 5.5 mM and acetoacetate 2 mM (see FIG. 3 from ref 63). Clearly, when ketone bodies are present in the blood at levels above 5 mM, they are able to substitute for the brain's usual need for glucose and abolish the hypoglycemic symptoms expected at blood glucose levels of 1.5 mM Ketone body utilization in brain is limited by the transport, with lesser utilization occurring in the basal ganglion at blood levels below 1 mM (76). However, at levels of 7.5 mM achieved in normal man by prolonged fasting, the rate of ketone body entry into brain is sufficient to take over the majority of cerebral energy needs and to prevent hypoglycemic symptoms, even in the face of blood sugar levels which would normally cause convulsions or coma (63).

It is the inventors hypothesis that in Alzheimer's disease, where there is a block at PDH which prevents the normal energy production from glucose, if one can provide elevated, eg. normal fasting levels of ketones, one can bypass the PDH blockade present in these patients thereby preventing cell death due to energy depletion or lack of cholinergic stimulation and thus slow the progression of the memory loss and dementia.

Furthermore, utilising the nerve growth/stimulatory effects of the ketone bodies, particularly D-β-hydroxybutyrate or a physiological ratio of this with acetoacetate, cells that are still viable can be caused to improve beyond the state to which they have degenerated and accordingly some improvement of function will be seen in patients.

In fed animals and in man the liver content, which is essentially that of blood, of acetoacetate is very low at 0.09 mM and D-β hydroxybutyrate is 0.123 mM but rises after a 48 hour fast to 0.65 mM acetoacetate and 1.8 mM D-β hydroxybutyrate (84). The ketone bodies rise in starvation because the fall in insulin decreases the re-esterification of fatty acids to triglyceride in adipose tissue causing the release of free fatty acids into the blood stream. The released free fatty acids can then be taken up and used as a source of energy by muscle, heart, kidney and liver in the process of β oxidation. Liver, however, has the capacity to convert the free fatty acids to a metabolic fuel, ketones, for use by extrahepatic organs, including the brain, as an alternative to glucose during periods of fasting. The hepatic synthesis of ketone bodies occurs from mitochondrial acetyl CoA generated during the β-oxidation of fatty acids by liver in the following set of reactions:

Acetyl CoA+Acetyl CoA$^{Mitochondrial\ Thialase>}$Actoacetyl CoA+ CoASH

Acetyl CoA+Acetoacetyl CoA+H$_2$O$^{Mitochondrial\ HMGCoA}$ $^{Synthase>}$HMGCoA HMGCoA$^{Mitochondrial\ HMGCoA\ Lyase>}$Acetoacetate+Acetyl CoASH Acetoacetate+NADH+H$^{+\beta Hydroxybutyrate}$ $_{Dehyrogenase>}$DβHydroxybutyrate+NAD$^+$ Once made in the liver, ketone bodies are transported out of the liver into the blood stream by the monocarboxylate —H' co-transporter (20) by the following reaction:

acetoacetate$^-_{inside}$+H$^+_{inside}$$^{Monocarboxylate\ Carrier>}$acetoacetate$^-_{outside}$+H$^-_{outside}$ The ketone bodies enter extra-hepatic tissues on the same carrier, where other monocarboxylates can act as competitive inhibitors. Unphysiological isomers such as D-lactate or L-β-hydroxybutyrate can also act as competitive inhibitors to ketone body transport. Since ketone body transport across the blood brain barrier is the limiting factor to ketone body utilization in brain (76) every effort should be made to keep the blood concentration of these unphysiological enantiomers at low levels during ketogenic therapy. When blood ketone body concentrations are elevated to levels found in starvation, heart, muscle, kidney and brain utilize ketone bodies as the preferred energy substrate:

Acetoacetate$^-$+Succinyl$^-$CoA$^{3-Oxoacid\ CoA\ Transferase>}$Acetoacetyl CoA+Succinate$^{2-}$ Acetoacetyl CoA+CoASH$^{Thiolase>}$2 Acetyl CoA Acetyl CoA+Oxaloacetate$^{2-Citrate\ Synthase>}$Citrate$^{3-}$+H$^+$ Citrate$^{3-}$>Krebs TCA cycle The present inventor has thus determined that the mitochondrial acetyl CoA from ketone bodies can thus replace the acetyl CoA deficiency which occurs during inhibition of PDH multienzyme complex in tissues dependent upon the metabolism of glucose for their supply of metabolic energy. The mitochondrial citrate supplied can also be transported to cytoplasm by the tri or dicarboxcylic acid transporter where it can be converted to cytoplasmic acetyl CoA required for the synthesis of acetyl choline. The reactions of the Krebs cycle are shown in Scheme 1 to help illustrate these concepts further.

The liver cannot utilize ketone bodies because it lacks the 3 Oxoacid CoA transferase necessary for the formation of acetoacetyl CoA. Ketone bodies, in contrast to free fatty acids, cannot produce acetyl CoA in liver. Since acetyl CoA is the essential precursor of fatty acid synthesis through malonyl CoA and cholesterol synthesis through cytosolic HMG CoA, ketone bodies cannot result in either increased fatty acid or cholesterol synthesis in liver, which usually accounts for over half of the bodies synthesis of these two potentially pathogenic materials. Liver is sensitive to the ratio of actoacetate/D-β-hydroxybutyrate presented to it and will alter its mitochondrial free [NAD$^+$]/[NADH], because of the near equilibrium established by ,β-hydroxybutyrate dehydrogenase (EC 1.1.1.30) (55)

SCHEME 1

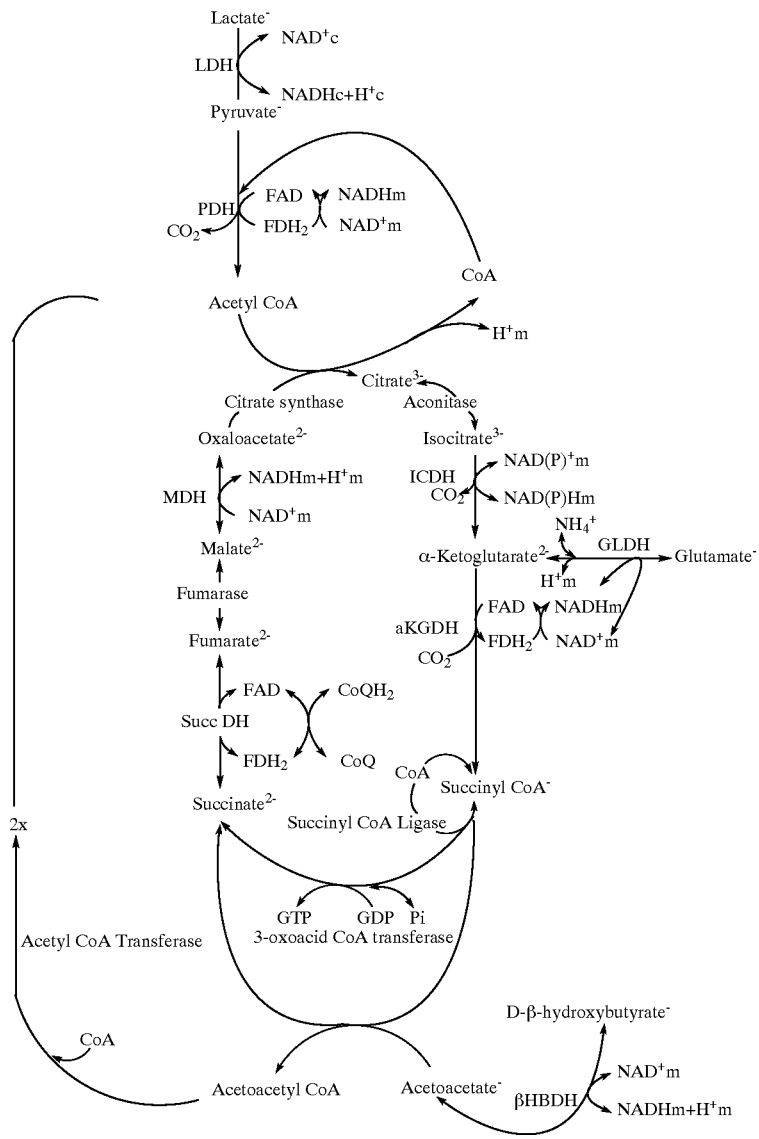

The easiest way to increase blood ketones is starvation. On prolonged fasting blood ketones reach levels of 7.5 mM (62, 63). However, this option is not available on a long term basis, since death routinely occurs after a 60 day fast.

The ketogenic diet, comprised mainly of lipid, has been used since 1921 for the treatment of epilepsy in children, particularly myoclonic and akinetic seizures (109) and has proven effective in cases refractory to usual pharmacological means (71). Either oral or parenteral administration of free fatty acids or triglycerides can increase blood ketones, provided carbohydrate and insulin are low to prevent re-esterification in adipose tissue.

Rats fed diets comprised of 70% corn oil, 20% casein hydrolysate, 5% cellulose, 5% McCollums salt mixture, develop blood ketones of about 2 mM. Substitution of lard for corn oil raises blood ketones to almost 5 mM (Veech, unpublished).

An example of a traditional 1500/day calorie ketogenic diet recommended by the Marriott Corp. Health Care Services, Pediatric Diet Manual, Revised August 1987 as suitable for a 4–6 year old epileptic child contained from 3:1 to 4:1 g of fat for each g of combined carbohydrate and protein. At each of 3 meals the patient must eat 48 to 50 g fat, only 6 g protein and 10 to 6.5 g carbohydrate. In practice this means that at each meal the child must eat 32 g of margarine per day (about ¼ stick) and drink 92 g of heavy cream (about 100 ml), comprised mainly as medium chain length triglycerides.

An example of a diet achieving a 3:1 ratio of fat to combined carbohydrate and protein is given in Table 1 below.

TABLE 1

Sample 1500 calorie diet to achieve 3:1 lipid to carbohydrate + protein diet

|  | Amount (g) | Fat (g) | Protein (g) | CHO (g) |
|---|---|---|---|---|
| Breakfast | | | | |
| Egg | 32 | 4 | 4 | |
| apple juice | 70 | | | 7 |
| margarine | 11 | 10 | | |
| heavy cream | 92 | 34 | 2 | 3 |
| Total Breakfast | | 48 | 6 | 10 |
| Lunch | | | | |
| lean beef | 12 | 1.75 | 3.5 | |
| cooked carrots | 45 | | 0.6 | 3 |
| canned pears | 40 | | | 4 |
| margarine | 14 | 12.5 | | |
| heavy cream | 92 | 34 | 2 | 3 |
| Total Lunch | | 48.25 | 6.1 | 10 |
| Supper | | | | |
| Frankfurter | 22.5 | 6 | 3 | |
| Cooked broccoli | 50 | | 1 | 2 |
| Watermelon | 75 | | | 5 |
| Margarine | 8 | 7.5 | | |
| Heavy cream | 92 | 34 | 2 | 3 |
| Total Supper | | 47.5 | 6 | 10 |
| Daily Total | | 143.75 | 18.1 | 30 |

In general the levels of ketone bodies achieved on such diets are about 2 mM D-β-hydroxbutyrate and 1 mM acetoacetate while the levels of free fatty acids about 1 mM. Other variations of composition have been tried including medium chain length triglycerides. In general compliance with such restricted diets has been poor because of their unpalatability (56). High lipid, low carbohydrate diets also have been tried as therapeutic agents in cancer patients to reduce glucose availability to tumors (88) as weight reducing diets in patients with and without diabetes (74, 112) to improve exercise tolerance (83).

The limitation of diets which rely upon lipid to raise blood ketones to neurologically effective levels are many. Firstly, levels of ketone bodies on lipid based diets tend to be below 3 mM, significantly lower than the level of 7.5 mM achieved in normal obese humans during prolonged fasting. Secondly, unauthorized ingestion of carbohydrate increases insulin secretion and causes a rapid decrease in the hepatic conversion of free fatty acids to ketones with a consequent drop in blood ketones and the diversion of lipid to esterified to triglycerides by adipose tissue. Many anecdotal reports relate the resumption of seizures in children who "broke their diet with birthday cake". Thirdly the unpalatability and the necessity to avoid carbohydrate to sustain high ketone body levels makes such high lipid diets difficult to use in adults in an out patient setting, particularly in societies where traditionally high intake of refined sugars, bread, pasta, rice and potatoes occurs. In practice, the traditional high ketone diet cannot be enforced in patients, other than children beyond the age where all food is prepared at home under strict supervision. Fourthly, ingestion of such large amounts of lipid in the adult population would lead to significant hypertriglyceridemia with its pathological sequelae of increased vascular disease and sporadic hepatic and pancreatic disease, and therefore could not be prescribed on medical grounds. Ingestion of high lipid, low carbohydrate diets were popular in the 1970s for weight reduction in the face of high caloric intake, provided that carbohydrate intake was low. However, because of the increased awareness of the relationship of elevated blood lipids to atherosclerosis the popularity of this diet dropped abruptly.

Supplementing a liquid diet with 47% of its caloric content with either glucose or racemic 1,3 butandiol caused the blood ketone concentration to rise about 10 fold to 0.98 mM D-β hydroxybutyrate and 0.33 mM acetoacetate (107). These values are slightly less than obtained normally in a 48 hour fast and far below the levels of 7.5 mM obtained in fasting man. Racemic 1,3 butandiol is converted by liver to acetoacetate and both the unnatural L-β and the natural D-β hydroxybutyrate (respectively (S) 3-hydroxybutanoate and (R) 3-hydroxybutanoate). Although racemic 1,3 butandiol has been extensively studied as a cheap caloric source in animal food and has even been used experimentally in human diets (81, 101) the production of the unnatural L-isomer is likely in the long run to produce significant toxicity as has been shown for the human use of the unnatural D-lactate (64). One disadvantage of administering the unnatural L isomer is that it competes for transport with the natural D-β hydroxybutyrate. Thus provision of the (R) 1,3 butandiol as a precursor of ketone bodies is one possibility that avoids unnecessary administration or production of the unnatural isomer.

The mono and diester of racemic 1,3 butandiol have been suggested as a source of calories and tested in pigs (67). Oral administration of a bolus of a diet containing 30% of calories as the esters produced brief peaks blood ketones to 5 mM. However, the use of racemic 1,3 butandiol with its production of the abnormal (S) 3-hydroxybutanoate is not to be recommended for the reasons stated above.

While use of racemic 1,3 butandiol in such formulations is not recommended, the esters of (R) 1,3 butandiol can be used, either alone or as the acetoacetate ester. (R) 1,3 butandiol may easily be synthesized by reduction of the monomeric D-β hydroxybutyrate, with for example $LiAlH_4$. (R) 1,3 butandiol is subject to being oxidized in the liver to form D-β hydroxybutyrate without marked distortion of the hepatic redox state. Studies in rats have shown that feeding racemic 1,3 butandiol caused liver cytosolic [NAD']/ [NADH] to decrease from 1500 to about 1000 (87). By comparison, administration of ethanol reduces hepatic [NAD-]/[NADH] to around 200 (106).

Acetoacetate, when freshly prepared, can be used in infusion solutions where it can be given in physiologically normal ratios to optimum effect (95). Because of manufacturing requirements which currently require long shelf life and heat sterilized fluids, acetoacetate has frequently been given in the form of an ester. This has been done to increase its shelf life and increase its stability to heat during sterilization. In the blood stream, esterase activity has been estimated to be about 0.1 mmol/min/ml and in liver about 15 mmol/min/g (68). In addition to esters combining 1,3 butandiol and acetoacetate there has also been extensive study of glycerol esters of acetoacetate in parenteral (59) and enteral nutrition (82). Such preparations were reported to decrease gut atrophy, due to the high uptake of acetoacetate by gut cells and to be useful in treatment of burns (85).

However, neither 1,3 butandiol, which forms acetoacetate, nor glycerol, which is a precursor of glucose, is part of the normal redox couple, D-β hydroxybutyrate/ acetoacetate. For the present invention, under optimum conditions, a physiological ratio of ketones should be given. If it is not, in the whole animal, the liver will adjust the ratio of ketones in accordance with its own mitochondrial free [$NAD^+$]/[NADH]. If an abnormal ratio of ketones is given pathological consequences are a distinct possibility. In the working heart, perfusion with acetoacetate as sole substrate, rapidly induces heart failure (99) in contrast to rat hearts perfused with a mixture of glucose, acetoacetate and D-β hydroxybutyrate, where cardiac efficiency was increased by a physiological ratio of ketone bodies (95).

The best exogenous source of ketone bodies, which do not require ingestion of large amounts of lipid nor the use of material which produce the physiologically incompatible isomers L-β-hydroxybutyrate would be ketone bodies themselves. However the present invention also provides alternatives for administration in therapy.

A first alternative are polyesters of D-β-hydroxybutyrate. Natural polyesters of D-β-hydroxybutyrate are sold as articles of commerce at polymers of 530,000 MW from Alcaligenes eutrophus (Sigma Chemical Co. St. Louis) or as 250,000 MW polymers for sugar beets (Fluka, Switzerland). The bacteria produce the polymer as a source of stored nutrient. The fermentation of these polymers by bacteria was developed in the 1970s by ICI in the UK and Solvay et Cie in Belgium, as a potentially biodegradable plastic for tampon covers and other uses. The system responsible for the synthesis of the poly D-β-hydroxybutyrate has now been cloned and variations in the composition of the polymer produced, based on the substrates given to the bacteria demonstrated. However, these polymers failed to be able to compete with petroleum based plastics. Nevertheless the genes responsible for the synthesis of polyalkanoates has been cloned and expressed in a number of micro-organisms (93, 102, 113) allowing for production of this material in a variety of organisms under extremely variable conditions.

Poly D-β-hydroxybutyrate comes in a number of forms from different biological sources as an insoluble white powder with little taste and no odour and is suitable for incorporation into compositions for oral or other means of administration. Esterases capable of breaking the ester bonds of this material are ubiquitous in plasma and most cells. These polymer are also easily split by alkaline hydrolysis in vitro to make a series of polymers culminating in the production of the monomer of MW 104, which is transported from gut to portal vein by the normal monocarboxylate transporter. Alternatively acid hydrolysis may be carried out using the published method referred to in the Fluka promotional material.

Preferred forms of D-β-hydroxybutyrate polymer are oligomers of that ketone body designed to be readily digestable and/or metabolised by humans or animals. These preferably are of 2 to 100 repeats long, typically 2 to 20 and most conveniently from 3 to 10 repeats long. It will be realised that mixtures of such oligomers may be employed with advantage that a range of uptake characteristics might be obtained.

Particularly preferred are cyclic oligomers of D-β-hydroxybutyrate, known as oligolides, having formula

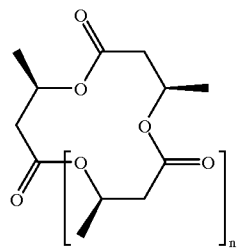

where n is an integer of 1 or more
or a complex thereof with one or more cations or a salt thereof Preferred cations are sodium, potassium, magnesium and calcium. Such cations are typically balanced by a physiologically acceptable counter-anion such that a salt is provided.

Examples of typical physiologically acceptable salts will be selected from sodium, potassium, magnesium, L-Lysine and L-arginine or eg. more complex salts such as those of methyl glucamine salts Preferably n is an integer from 1 to 200, more preferably from 1 to 20, most preferably from 1 to 10 and particularly conveniently is 1, ie. (R, R, R)-4, 8, 12-trimethyl-1, 5, 9-trioxadodeca-2, 6, 10-trione, 2, 3, 4 or 5.

Cyclic oligomers for use in the invention may be provided, inter alia, by methods described by Seebach et al. Helvetia Chimica Acta Vol 71 (1988) pages 155–167, and Seebach et al. Helvetia Chimica Acta, Vol 77 (1994) pages 2007 to 2033. For some circumstances such cyclic oligomers of 5 to 7 or more (R)-3-hydroxybutyrate units may be preferred as they may be more easily broken down in vivo. The methods of synthesis of the compounds described therein are incorporated herein by reference.

In preferred forms of all of the aspects of the invention, where the oligomer of of D-β-hydroxybutyrate does not include acetoacetyl groups it is optionally and preferably administered together with a physiological ratio of acetoacetate or a metabolic precursor of acetoacetate.

Once the monomer is in the blood stream, and since liver is incapable of metabolizing ketone bodies but can only alter the ratio of D-β-hydroxybutyrate/acetoacetate, the ketone bodies are transported to extrahepatic tissues where they can be utilized. The blood levels of ketones achieved are not be subject to variation caused by noncompliant ingestion of carbohydrate, as is the case with the present ketogenic diet. Rather, they would simply be an additive to the normal diet, given in sufficient amounts to produce a sustained blood level, typically of between 0.0.3 to 20 mM, more preferably 2 to 7.5 mM, over a 24 hour period, depending upon the condition being treated. In the case of resistant childhood epilepsy, blood levels of 2 mM are currently thought to be sufficient. In the case of Alzheimer's disease, attempts could be made to keep levels at 7.5 mM achieved in the fasting man studies, in an effort to provide alternative energy and acetyl CoA supplies to brain tissue in Alzheimer's patients where PDH capacity is impaired because of excess amounts of $A\beta_{1-42}$ amyloid peptide (77, 78).

The determination by the inventor that D-β-hydroxybutyrate and its mixtures with acetoactetate act as a nerve stimulant, eg. nerve growth stimulant and/or stimulant of axon and dendritic growth, opens up the option of raising ketone body levels to lesser degrees than required nutritionally in order to treat neurodegeneration.

Compositions of the invention are preferably sterile and pyrogen free, particularly endotoxin free. Secondly, they are preferably formulated in such a way that they can be palatable when given as an additive to a normal diet to improve compliance of the patients in taking the supplements. The oligomers and polymers are generally taste and smell free. Formulations of D-β-hydroxybutyrate and its mixtures with acetoacetate may be coated with masking agents or may be targeted at the intestine by enterically coating them or otherwise encapsulating them as is well understood in the pharmaceuticals art.

Since ketone bodies contain about 6 calories/g, there is preferably a compensatory decrease in the amounts of the other nutrients taken to avoid obesity.

Particular advantages of using the ketone bodies or precursors such as poly or oligo-D-β-hydroxybutyrate or acetoacetate esters are:

1) they can be eaten with a normal dietary load of carbohydrate without impairing its effects,
2) they will not raise blood VLDL, as with current cream and margarine containing diets, thus eliminating the risk of accelerated vascular disease, fatty liver and pancreatitis,
3) they will have a wider range of use in a greater variety of patients, including: type II diabetes to prevent hypoglycemic seizures and coma, in Alzheimer's disease and other neurodegenerative states to prevent death of nerve cells eg. hippocampal cells, and in refractory epilepsy due to either decreases in cerebral glucose transporters, defects in glycolysis, or so called Leigh's syndromes with congenital defects in PDH.

The second group of particular alternatives are acetoacetate esters of D-β-hydroxybutyrate. Esters which provide a physiological ratio of acetoacetate to D-β-hydroxybutyrate are preferred eg. from 1:1 to 1:20, more preferably from 1:1 to 1:10. The tetramer of D-β-hydroxybutyrate with a terminal acetoacetate residue is particularly preferred. Such materials have the added virtue of having a physiological ratio of D-β-hydroxybutyrate/acetoacetate moieties, thus removing the burden on liver of having to adjust the redox state of the administered nutrient without inducing abnormal reduction of hepatic [NAD$^+$]/[NADH] as occurs with excessive alcohol consumption. The polymeric esters, depending upon their length, have decreasing water solubility, but are heat stable. Such polymers can for example be used in oral and parenteral use in emulsions, whereas acetoacetate, in the unesterified state, is less preferred as it is subject to spontaneous decarboxylation to acetone with a half time at room temperature of about 30 days.

Examples of poly D-β-hydroxybutate or terminally oxidized poly D-β-hydroxybutyrate esters useable as ketone body precursors are given below.

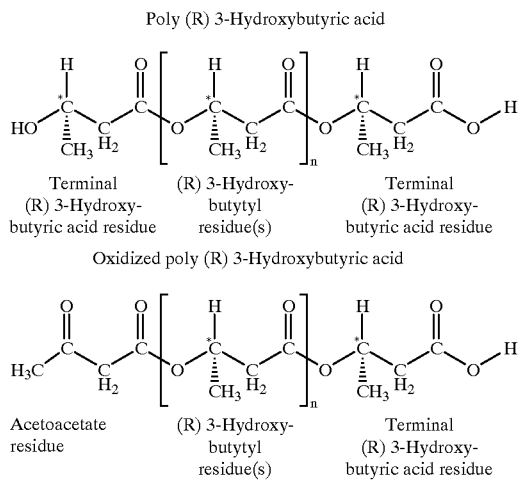

Poly (R) 3-Hydroxybutyric acid

Terminal (R) 3-Hydroxybutyric acid residue | (R) 3-Hydroxybutytyl residue(s) | Terminal (R) 3-Hydroxybutyric acid residue Oxidized poly (R) 3-Hydroxybutyric acid Acetoacetate residue | (R) 3-Hydroxybutytyl residue(s) | Terminal (R) 3-Hydroxybutyric acid residue In each case n is selected such that the polymer or oligomer is readily metabolised on administration to a human or animal body to provide elevated ketone body levels in blood. Preferred values of n are inetegers of 0 to 1,000, more preferably 0 to 200, still more preferably 1 to 50 most preferably 1 to 20 particularly conveniently being from 3 to 5.

A number of variations of this material, including the polyester D-β-hydroxybutyrate itself can also be tried for suitable manufacturing characteristics. The material is a tasteless white powder After partial alkaline hydrolysis, a mixture of varying chain length polymers would be provided, which would tend to smooth gut absorption and maintain high sustained levels of ketone over a 24 hour period.

Treatment may comprise provision of a significant portion of the caloric intake of patients with the D-β-hydroxybutyrate polyester formulated to give retarded release, so as to maintain blood ketones in the elevated range, eg. 0.5 to 20 mM, preferably 2–7.5 mM, range over a 24 hour period. Release of the ketone bodies into the blood may be restricted by application of a variety of techniques such as microencapsulation, adsorption and the like which is currently practised in the oral administration of a number of pharmaceutical agents. Enetrically coated forms targeting delivery post stomach may be particularly used where the material does not require hydrolysis in acid environment. Where some such hydrolysis is desired uncoated forms may be used. Some forms may include enzymes capable of cleaving the esters to release the ketone bodies such as those referred to in Doi. Microbial Polyesters.

Intravenous infusion of sodium salts of D-β-hydroxybutyrate has been performed on normal human subjects and patients for a number of conditions, eg. those undergoing treatment for severe sepsis in an intensive care unit. It was found to be non-toxic and capable of decreasing glucose free fatty acids and glycerol concentration, but ineffective in decreasing leucine oxidation.

The monomer of D-β-hydroxybutyrate is a white, odourless crystal with a slightly tart or acid taste which is less in intensity in comparison to vinegar or lemon juice. It can be formulated into most foodstuffs, eg. drinks, puddings, mashed vegetables or inert fillers. The acid forms of D-β-hydroxybutyrate are suitable for use orally as they have a pKa of 4.4. This is less acid than citric acid with pKa1 of 3.1 and pKa2 of 4.8 and slightly more acidic than acetic acid with a pKa of 4.7.

Preferably, only the natural D- or (R) isomer is used in this formulation. Since in practice it is not possible to achieve absolute isomeric purity, the article of commerce currently sold by Sigma, St. Louis, Mo. or Fluka, Ronkonkoma, N.Y. is the most suitable for this purpose. The optical rotation of the commercially available D-β-hydroxybutyric acid is $-25°\pm 1$ at the wavelength of Na and its melting point 43–46° C. The optical rotation of the Na salt of D-β-hydroxybutyrate is $-14.5°$ and its melting point 149–153° C. Both can be assayed by standard enzymatic analysis using D-β-hydroxybutyrate dehydrogenase (EC 1.1.1.30)(5). Acetoacetate can be determined using the same enzyme (56). The unphysiological (S) isomer is not measurable with enzymatic analysis but can be measured using GC mass spec (13).

For a 1500 calorie diet, the human adult patient could consume 198 g of ketones per day. For a 2000 calorie diet of the same proportions, one could consume 264 g of ketones per day. On the ketogenic lipid diet blood ketones are elevated to about 2 mM. On the ketone diet, ketone levels should be higher because ketones have been substituted at the caloric equivalent of fat, that is 1.5 g of ketone/1 g of fat. Accordingly, blood ketones should be approximately 3 mM, but still below the level achieved in fasting man of7.5 mM.

The advantage of using ketone bodies themselves are several. Firstly, provision of ketone bodies themselves does not require the limitation of carbohydrate, thus increasing the palatability of the dietary formulations, particularly in cultures where high carbohydrate diets are common. Secondly, ketone bodies can be metabolized by muscle, heart and brain tissue, but not liver. Hence the fatty liver, which may be an untoward side effect of the ketogenic diet, is avoided. Thirdly, the ability to include carbohydrate in the dietary formulations increases the chance of compliance and opens up practical therapeutic approaches to type II diabetics where insulin is high, making the known ketogenic diet unworkable.

The present inventor has determined that, while any elevation of ketone bodies may be desirable, a preferred amount of ketone bodies to be administered will be sufficient to elevate blood levels to the 0.5 to 20 mM level, preferably to the 2 mM to 7.5 mM level and above, particularly when attempting to arrest the death of brain cells in diseases such as Alzheimer's. While dead cells cannot be restored, arrest of further deterioration and at least some restoration of function is to be anticipated.

Thus in a first aspect of the present invention there is provided the use acetoacetate, D-β-hydroxybutyrate or a metabolic precursor of either in the manufacture of a medicament or nutritional aid (i) for increasing cardiac efficiency, particularly efficiency in use of glucose (ii) for providing energy source, particularly in treating diabetes and insulin resistant states or by increasing the response of a body to insulin (iii) for reversing, retarding or preventing nerve cell damage or death related disorders, particularly neurodegenerative disorders such as memory associated disorders such as Alzheimer's, seizure and related states such as encepalophies such as CJD and BSE.

The term metabolic precursor thereof particularly relates to compounds that comprise 1,3-butandiol, acetoacetyl or D-β-hydroxybutyrate moieties such as acetoacetyl-1,3-butandiol, acetoacetyl- D-β-hydroxybutyrate, and acetoacetylglycerol. Esters of any such compounds with monohydric, dihydric or trihydric alcohols is also envisaged.

This aspect includes such use as a neuronal stimulant eg capable of stimulating axonal and/or dendritic growth in nerve cells, eg. in Hippocampus or Substantia nigra particularly in diseases where neurogeneration has serious clinical consequences.

In diabetic patients this use of these compounds allows maintenance of low blood sugar levels without fear of hypoglycemic complications. In normal non-diabetic subjects the fasting blood sugar is 80 to 90 mg % (4.4–5 mM) rising to 130 mg % (7.2 mM) after a meal. In diabetics 'tight control' of diabetes has long been recommended as a method for retardation of vascular complications but, in practice, physicians have found it difficult to keep blood sugars tightly controlled below 150 mg % (8.3 mM) after eating because of hypoglycaemic episodes. Hypoglycaemic coma occurs regularly in normal subjects whose blood sugar drops to 2 mM. As discussed earlier, (62, 63) in the presence of 5 mM blood ketones there are no neurological symptoms when blood sugars fall to below 1 mM.

The present inventor has determined that supplementing type II diabetics with ketone bodies would allow better control of blood sugar, thus preventing the vascular changes in eye and kidney which occur now after 20 years of diabetes and which are the major cause of morbidity and mortality in diabetics.

Where the therapy is aimed at seizure related disorders, such as refractory epilepsy as is treated by the ketogenic diet, therapy is improved by use of ketone bodies, their polymers or esters or precursors such as butandiol compounds, due to the reduction or elimination of high lipid and carbohydrate content. Such patients include those with genetic defects in the brain glucose transporter system, in glycolysis or in PDH itself such as in Leigh's syndrome.

Particular disorders treatable with these medicaments are applicable to all conditions involving PDH blockage, including those conditions occuring after head trauma, or involving reduction or eleimination of acetyl CoA supply to the mitochondrion such as insulin coma and hypoglycaemia, defects in the glucose transporter in the brain or in glycolytic enzyme steps or in pyruvate transport.

Preferably the hydroxybutyrate is in the form of non-racemic D-β-hydroxybutyrate and more preferably it is administered in a form which also supplies acetoacetate. Preferably the metabolic precursor is one which when administered to a human or animal body is metabolised, eg. by liver, to produce one or both of D-β-hydroxybutyrate and acetoacetate, more preferably in a physiological ratio. Particularly preferred are poly-D-β-hydroxybutyric acid or acetoacetoyl-β-hydroxybutyrate oligomers or an ester of one or both of these. Lower alkyl esters such as $C_{1-4}$ alkyl esters may be employed but more preferably are more physiologically acceptable esters such as the respective 1,3-butandiol esters, particularly employing (R)-1,3-butandiol. Most preferred are the acetoacetyl- tri-, tetra- and penta- D-β-hydroxybutyrate esters. Ester precursors will include esters of 1,3-butandiol, preferably (R) form and particularly acetoacetate esters such as acetoacetyl glycerol.

Preferred poly D-β-hydroxybutyrate esters are those which are esters of the preferred oligomers of 2–100 repeats, eg. 2–20 repeats most preferably 2–10 repeats.

Where the medicament or nutritional product of the invention is for use without prolonged storage it is convenient to use it in the form of a liquid or solid composition comprising the hydroxy substituted carboxylic acid and/or the ketone, preferably comprising both and where these are the D-β-hydroxybutyrate acids and acetoacetate together preferably in the ratio of about 3:1 to 5:1, more preferably about 4:1.

Where the medicament or aid comprises acetoacetate it is preferably not stored for a prolonged period or exposed to temperatures in excess of 40° C. Acetoacetate is unstable on heating and decomposes violently at 100° C. into acetone and $CO_2$. In such circumstances it is preferred that acetoacetate is generated by the composition on contact with the bodies metabolic processes. Preferably the composition comprises an ester precursor of actetoacetate. For example, the ethyl ester of acetoacetate is relatively stable with a boiling point of 180.8° C.

Still more preferably, the medicament or aid comprises an acetoacetyl ester of D-β-hydroxybutyrate or such an ester of an oligomer of D-β-hydroxybutyrate as described. This may be supplemented with D-β-hydroxybutyrate or one of the polymers of that, e.g. oligo-D-β-hydroxybutyrate, in order to bring about the preferred ratio of the two components. Such a composition will provide the two preferred components when the ester and polymer are metabolised in the stomach or in the plasma of the human or animal which has consumed them. Again an (R) 1,3-butandiol ester of the acetoacetyl-D-β-hydroxybutyrate may be most preferred as it will be more lipophilic until metabolised or otherwise deesterified and all its components are convereted to the desired ketone bodies.

A second aspect of the invention provides novel esters of acetoacetate for use in therapy or as a nutritional aid. Such esters may include $C_{1-4}$ alkyl esters but most preferred are the D-β-hydroxybutyryl-acetoacetate esters referred to above.

A third aspect of the present invention provides a poly-D-β-hydroxybutyrate for use in therapy, particularly where this is in a form selected for its ability to be degraded in acid conditions of the stomach or by esterases in vivo.

A fourth aspect of the invention provides a method for the synthesis of D-β-hydroxybutyryl-acetoacetate esters comprising the reaction of acetoacetic acid halide, e.g. acetoacetyl chloride, with D-β-hydroxybutyrate. Preferably this is achieved by reacting acetoacetic acid with an activating agent, such as thionyl chloride, to produce the acid chloride.

A fifth aspect of the present invention provides a method for the synthesis of D-β-hydroxybutyryl-acetoacetate esters comprising the reaction of D-β-halobutyrate or its oligomers with acetoacetic acid, activated forms thereof or diketene.

A sixth aspect of the present invention provides a D-β-hydroxybutyryl-acetoacetate ester per se, a physiologically acceptable salt or short or medium chain mono, di or trihydric alcohol or 1,3-butandiol estsr thereof.

A seventh aspect of the present invention provides poly-D-β-hydroxybutyrate together with a pharmaceutically or physiologically acceptable carrier.

An eighth aspect of the present invention provides a composition comprising D-β-hydroxybutyrate and acetoacetic acid in a ratio of from 1;1 to 20:1, more preferably 2:1 to 10:1 and most preferably from 3:1 to 5:1 together with a pharmaceutically or physiologically acceptable carrier. Preferably the ratio of these components is about 4:1. Such a composition does not consist of plasma, serum or animal or plant tissue already used as a medicament or foodstuff, thus it is that which is preferably sterile and pyrogen free. Particularly the ketone bodies comprise at least 5% of the composition by weight, more preferably 20% or more and most preferably 50% to 100%. The composition may be adapted for oral, parenteral or any other conventional form of administration.

A ninth aspect of the present invention comprises a method of treating a human or animal in order to increase their cardiac efficiency comprising administering to that person at least one of a materials for use in the first to eight aspects of the invention.

A tenth aspect of the present invention comprises a method of treating a human or animal in order to increase their the response to insulin comprising administering to that person at least one of a materials for use in the first to eight aspects of the invention.

An eleventh aspect of the present invention comprises a method of treating a human or animal in order to treat an insulin resistant state comprising administering to that person least one at least one of a materials for use in the first to eight aspects of the invention.

By insulin resistant state herein is included forms of diabetes, particularly those that do not respond fully to insulin.

A twelvth aspect of the invention provides a method of treating a human or animal in order to treat a nerve cell, eg. brain cell, death or damage related disorder as referred to for the first aspect, particularly a neurodegenerative disorder eg. such as those related to neurotoxic conditions such as presence of amyloid protein, eg. a memory associated disorder such as Alzheimer's disease, or epileptic seizures, comprising administering to that person least one at least one of a materials for use in the first to eight aspects of the invention.

Preferred methods of the ninth to twelvth aspects of the invention use the preferred ketones and polyacids and acid esters of the invention.

Methods of preparing poly D-β-hydroxybutyrate are not specifically claimed as these are known in the art. For example Shang et al, (1994) Appli. Environ. Microbiol. 60: 1198–1205. This polymer is available commercially from Fluka Chemical Co. P1082, cat#81329, 1993–94, 980. Second St. Ronkonkoma, N.Y. 11779-7238, 800 358 5287.

Particular advantages of use of the biologically available polymers of the invention include the reduction in the amount of counter ions such as sodium that have to be coadministered with them. This reduction in sodium load is advantageous particularly in ill health. By biologically available is meant those materials which can be used by the body to produce the least one of a D-β-hydroxybutyrate, acetoacetate and a mixture of these in physiological ratio as described above The amount of ketone bodies used in treatment of neurodegeneration such as Alzheimer's and Parkinsonism will preferably elevate blood levels to 0.5 mM to 20 mM, eg 2 mM to 7.5 mM as described above. The present inventor estimates that 200 to 300 g (0.5 pounds) of ketone bodies per patient per day mignt be required to achieve this. Where the treatment is through maintenance of cells against the effects of neurotox in this may be at a higher level, eg. 2 to 7.5 mM in blood. Where it relies on the nerve stimulatory factor effect of the D-β-hydroxybutrrate so produced the amount administered may be lower, eg. to provide 0.2 to 4 mM, but can of course be more for this or other disease.

It will be realised that treatment for neurodegenerative diseases such as Alzheimer's will most effectively be given soon after identifying patient's with a predisposition to develop the disease. Thus treatment for Alzheimers's most effectively follows a positive test result for one or more conditions selected from the group (i) mutations in the amyloid precursor protein gene on chromosome 21, (ii) mutations in the presenilin gene on chromosome 14, (iii) presence of isoforms of apolipoprotein E. Other tests shown to be indicative of Alzheimer's will of course be applicable.

Following such a positive test result it will be appropriate to prevent the development of memory loss and/or other neurological dysfunction by elevation of the total sum of the concentrations of the ketone bodies D-β-hydroxybutyrate and acetoacetate in the patient's blood or plasma to say between 1.5 and 10 mM, more preferably 2 to 8 mM, by one of several means. Preferably the patient is fed a diet of sufficient quantities of D-β-hydroxybutrate, its metabolisable polymers, its acetoacetate esters or their precursors (R)-1,3-butandiol and its acetoacetate esters, eg. acetoacetyl glycerol, or its administered intravenously or intrarterially the ketone bodies D-β-hydroxybutyrate and acetoacetic acid. All of the organic materials referred to above are optionally in salt or ester form. Examples of typical physiologically acceptable salts will be selected from sodium, potassium, magnesium, L-Lysine and L-arginine or eg. more complex salts such as those of methyl glucamine salts. Esters will be those as described previously for other aspects of the invention.

A still further aspect of the invention provides the ketone bodies of the invention by suitable control of diet. Thus this aspect provides a method of treatment of a human or animal for a disorder of one or more of the ninth to the twelvth aspects of the invention comprising one of (i) total fasting of the individual and (ii) feeding the individual a ketogenic diet eg. of 60–80% lipid with carbohydrate content 20% or less by weight.

For the purpose of treaing seizures, eg. in epilepsy, a diet may involve ad lib ingestion of carbohydrate by oral or enteral route or of the compounds specified above.

In all these treatments other than the ketogenic diet there is the improvement that a method of avoiding drop in blood ketones which accompanies the ingestion of excess carbohydrate and a method which avoids feeding of excess lipid which accelerates the synthesis by liver of fatty acids and cholesterol which would otherwise contribute to vascular disease.

It will be realised that hypoglycemic brain dysfunction will also be treatable using the treatments and compositions and compounds of the present invention. A further property associated with the present treatment will be general improvement in muscle performance.

The provision of ketone body based foodstuffs and medicaments of the invention is faciliated by the ready availability of a number of relatively cheap, or potentially cheap, starting materials from which (R)-3-hydroxybutyric acid may be derived (see Microbial Polyesters Yoshiharu Doi. ISBN 0-89573-746–9 Chapters 1. 1, 3.2 and 8). The availability of genes capable of insertion into foodstuff generating organisms provides a means for generating products such as yoghurts and cheese that are enriched in either poly-(R)-3-hydroxybutyric acid or, after breakdown with enzmes capable of cleaving such polymers, with the monomeric substance itself (see Doi. Chapter 8).

The present invention will now be described further by way of illustration only by reference to the following Figures and experimental examples. Further embodiments falling within the scope of the invention will occur to those skilled in the art in the light of these.

FIGURES

EXAMPLES

Example 1

Figure 1:
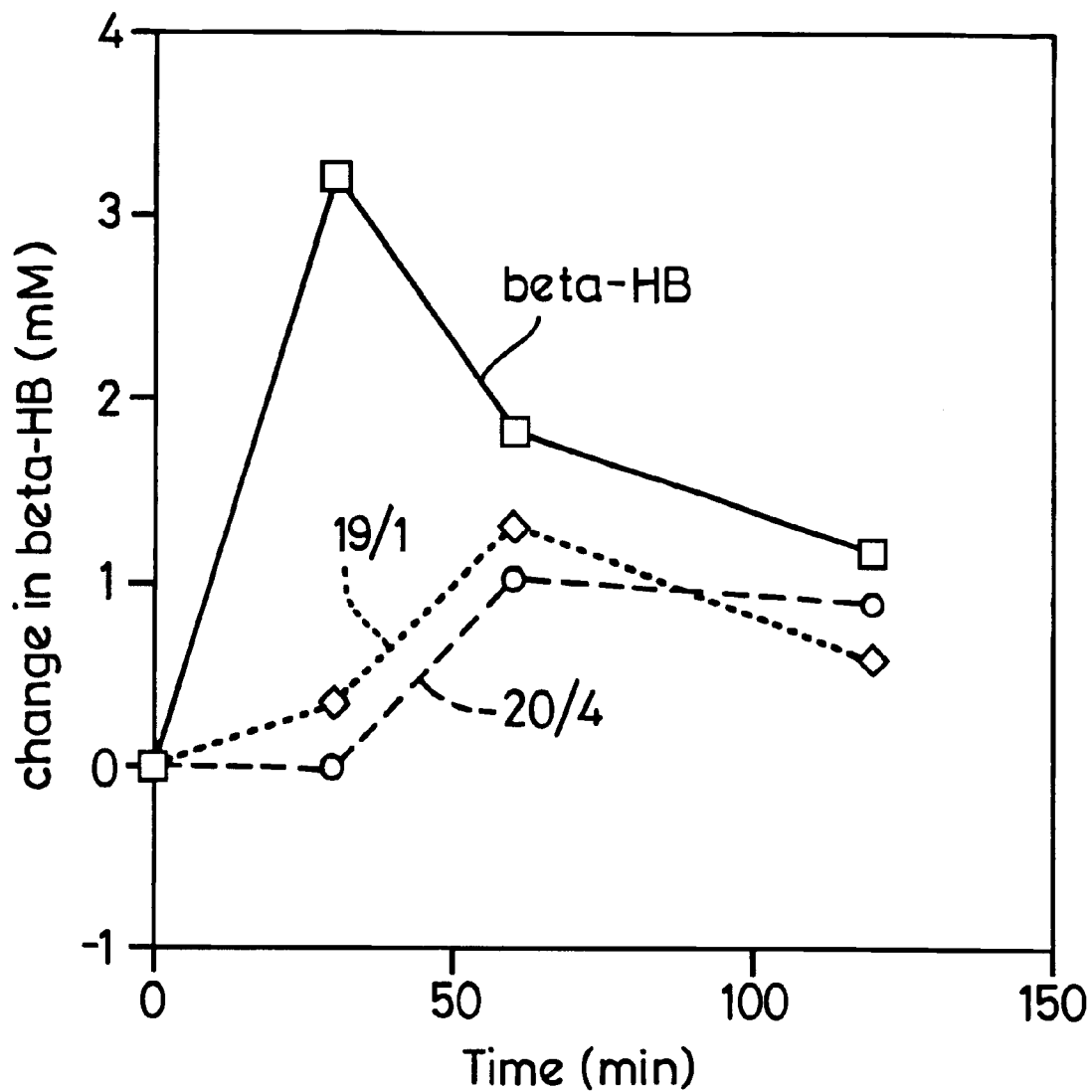
FIG. 1 is a graph showing blood (R)-3-hydroxybutyrate level produced after time after gavage of (R)-3-hydroxybutyrate, an oligomer of this as produced in Example 1 and an acetoacetyl monomer therof as produced in Example 2.
Figure 2:
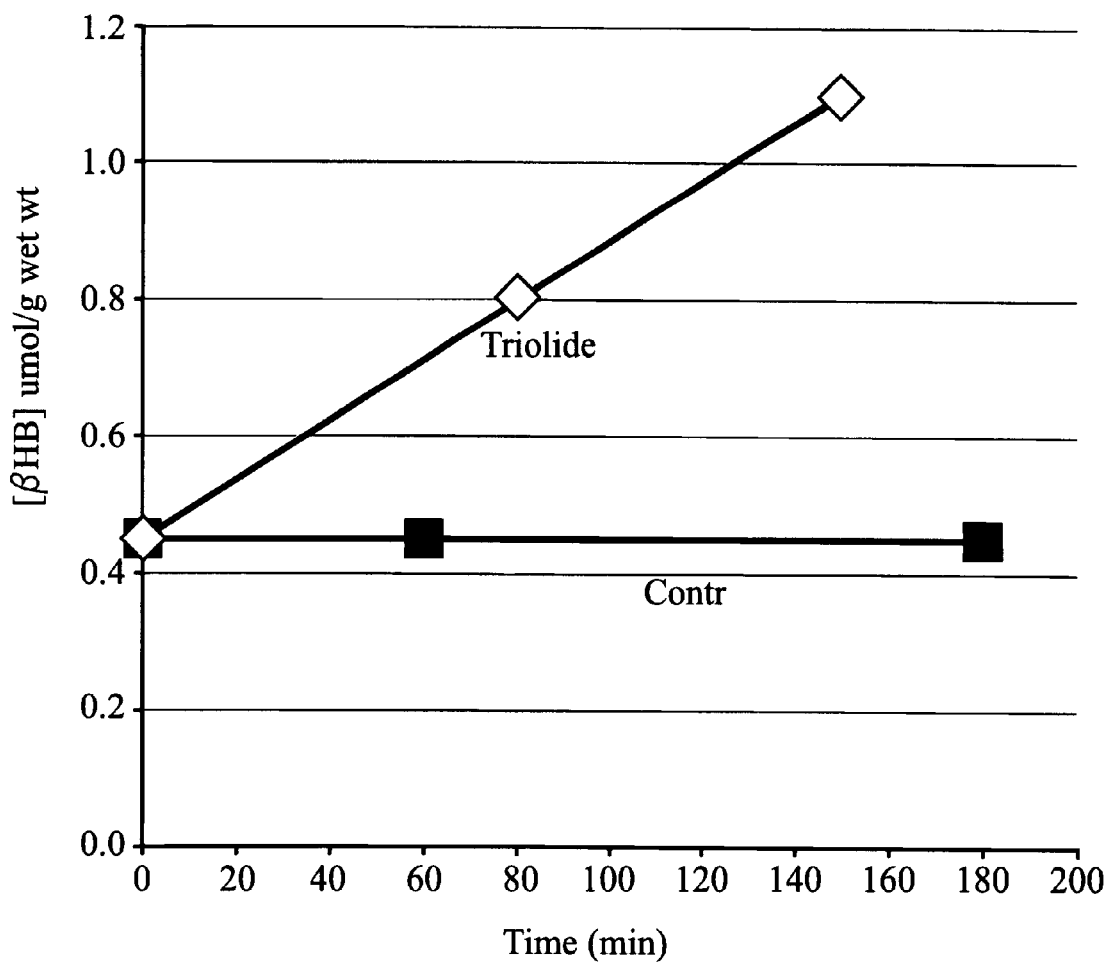
FIG. 2 is a graph showing blood (R)3-hydroxybutyrate level produced after time after feeding rats with the triolide of (R)-3-hydroxybutyrate, a cyclic oligomer produced in Example 1 in yoghurt and controls fed yoghurt alone.

Preparation of Oligomers of (R)-3-hydroxybutyric acid (D-β-hydroxybutyrate)

(R )-3-hydroxybutyric acid (Fluka-5.0 g: 0.048 mole), p-toluene sulphonic acid (0.025 g) and benzene (100 ml) were stirred under reflux withn a Dean-Stark trap arrangement for 24 hours. The reaction mixture was cooled and the benzene evaporated in vacuo (0.5 mm Hg). 4.4 g of colourless oil was obtained of which a 20 mg sample was converted to the methyl ester for analysis of number of monomer repeats using NMR. These studies show that the product is a mixture of oligomers of D-β-hydroxybutyrate of avaerage number of repeats 3.75, being mainly a mixture of trimers, tetramers and pentamers with the single most abundant material being the tetramer. The product mixture was soluble in 1 equivalent of sodium hydroxide.

Example 2

Preparation of Acetoacetyl Ester of Oligomeric (R)-3-hydroxybutyric Acid.

A further batch of the colourless oil product from Example 1 (4.5 g) was heated for 1 hour at 60° C. with diketene (3.8 g) and sodium actetate (0.045 g) under nitrogen. Further diketene (3.8 g) was added and the reaction heated for a further hour, cooled and diluted with ether, washed with water and then extracted with saturated sodium bicarbonate (5×100 ml). Combined extract was washed with ether then acidified with concentrated HCl (added dropwise). Ethyl acetate extraction (3×50 ml) was followed by drying over magnesium sulphate and evaporation in vacuo. A yellow solid/oil mixture was obtained (7.6 g) which was chromatographed on a silica column using dichloromethane/methanol (98:2) to give a light amber oil product. Faster moving impurities were isolated (1.6 g) and after recolumning carbontetrachloride/methanol (99:1) 0.8 g of oil was recovered which was shown by NMR and Mass spectrometry to be the desired mixture of acetoacetylated oligomers of D-β-hydroxybutyrate. The product mixture had an Rf of 0.44 in dichloromethane/methanol (90:1) and was soluble in 1 equivalent of sodium hydroxide. Both products of Example 1 and Example 2 are susceptible to separation of individual components by preparative HPLC.

Example 3

Oral Administration of D-βhydroxybutyrate, Oligomers and Acetoacetyl D-β-hydroxybutyrate Oligomers to Rats The ability of orally administered D-βhydroxybutyrate and the oligomers of Examples 1 and 2 to raise blood ketone body levels was investigated as follows. Rats were starved overnight and then gavaged with 100 μl/100 g bodyweight of 4M D-β-hydroxybutyrate brought to pH 7.74 using methyl glucamine. Blood levels of D-β-hydroxybutyrate measured using and NAD+/EDTA assay of Anal. Biochem. 131, p478–482 (1983). 1.0 ml of a solution made up from 2-amino-2-methyl-1-propanol (100 mM pH 9.9, 0.094 g/10 ml), NAD+(30 mM, 0.199 g/10 ml) and EDTA (4 mM, 0.015 g/10 ml) was added to each of a number of cuvettes and 4 μl sample or D-β-hydroxybutyrate control.

As the rats had been fasted the initial levels of D-β-hydroxybutyrate were elevated from the 0.1 mM fed state. However, consistent serum increases of D-β-hydroxybutyrate, between 1 and 3.2 mM increase in each case, were provided.

This procedure was repeated with 2M solutions of the mixtures of D-β-hydroxybutyrate oligomers and their acetoacetyl esters described in Examples 1 and 2. The D-β-hydroxybutyrate oligomer (19/1 in FIG. 1) and the acetoacetyl ester (20/4 in FIG. 1) were both brought to pH 7.6 with methyl glucamine and the blood D-β-hydroxybutyrate level monitored using the aforesaid assay procedure. Increases in serum D-β-hydroxybutyrate were shown to be of 0.5 to 1.2 mM at 60 and 120 minutes after gavaging. These results demonstrate the efficacy of orally administered D-β-hydroxybutyrate and its metabolic precursors of the invention in raising blood levels significantly for a period of hours after intake.

It was noted that the oligomeric esters 19/1 and 20/4, while not elevating the blood ketone body level as high as the monomer itself, did result in elevation for a much longer period of time and thus are suited to adminsitration less frequently than the monomer.

Example 4

TABLE 2

Sample 1500 calorie ketogenic diet using ketone bodies, their esters or polymers. The ketones were assumed to contain 6 kcal/g, fats 9 kcal/g, carbohydrate and protein 4 kcal/g. Ketones have been substituted to give equivalent calories.

| | Amount (g) | Fat (g) | Protein (g) | CHO (g) | Ketones (g) |
|---|---|---|---|---|---|
| Breakfast | | | | | |
| Egg | 32 | 4 | 4 | | |
| apple juice | 70 | | | 7 | |
| ketones | 66 | | | | 66 |
| skim milk | 92 | 0 | 2 | 3 | |
| Total Breakfast | | 4 | 6 | 10 | 66 |
| Lunch | | | | | |
| Lean beef | 12 | 1.75 | 3.5 | | |
| cooked carrots | 45 | | 0.6 | 3 | |
| canned pears | 40 | | | 4 | |
| ketones | 69.75 | | | | 69.75 |
| skim milk | 92 | | 2 | 3 | |
| Total Lunch | | 1.75 | 6.1 | 10 | 69.75 |
| Supper | | | | | |
| Frankfurter | 22.5 | 6 | 3 | | |
| cooked broccoli | 50 | | 1 | 2 | |
| watermelon | 75 | | | 5 | |
| ketones | 62.25 | | | | 62.25 |
| skim milk | 92 | | 2 | 3 | |
| Total Supper | | 6 | 6 | 10 | 62.25 |
| Daily Total | | 11.75 | 18.1 | 30 | 198 |

Example 5
Effect of Increased Blood D-β-hydroxybutyrate Levels on Whole Brain GABA Levels To assess the effect of D-β-hydroxybutyrate on whole brain GABA levels, and thus provide an indication of antiepileptic effect of ketone body or precursor treatment aimed at increasing blood ketone body levels, whole rat brain was frozen at set times after administration of D-β-hydroxybutyrate as described in Example 3. GABA was assayed using standard HPLC technique and related to protein content using standard protein assay. At t=0 GABA levels were 191 pmoles/μg protein while at 120 minutes this was elevated at 466 pmoles/μgprotein, demonstrating antepileptic potential.

Example 6
Effect of D-β-hydroxybutyrate on β-amyloid Toxicity to Hippocampal Cells in Vitro Culture Medium and Chemicals The serum free medium used from 0 to day 4 contained Neurobasal medium with B27 supplement diluted 50 fold (Life Technology, Gaithersburg, Md.) to which was added: 0.5 mM L-glutamine, 25 μM Na L-glutamate, 100 U/ml penicillin and 100 μg/ml streptomycin. After day 4, DMEM/F12 medium containing 5 μM insulin, 30 nM 1-thyroxine, 20 nM progesterone, 30 nM Na selenite 100 U/ml penicillin and 100 μg/ml streptomycin were used.

Hippocampal Microisland Cultures

The primary hippocampal cultures were removed from Wistar embryos on day 18 and dispersed by gentle aggitation in a pipette. The suspension was centrifuge at 1,500×g for 10 min and the supernatant discarded. New media was make 0.4–0.5×10$^6$ cells/ml. Ten μl of this suspension was pipetted into the center of poly D-lysine coated culture wells and the plates incubated at 38° C. for 4 hrs and then 400 μl of fresh Neurobasal media was added. After 2 days of incubation, half of the media was exchanged for fresh media and the incubation continued for 2 more days. After day 4, the medium was changed with DMEM/F12 medium containing 5 μM insulin, 30 nM 1-thyroxine, 20 nM progesterone, 30 nM Na selenite 100 U/ml penicillin and 100 μg/ml streptomycin. The wells were divided into 4 groups: half the wells received Na D-β-hydroxybutyrate to a final concentration of 8 mM while and half of the wells received 5 nM amyloid $β_{1-42}$ (Sigma). These media were exchanged 2 days later (day 8) and the cells were fixed on day 10 and stained with anti MAP2 (Boehringer Manheim, Indianapolis, Ind.) to visual neurons and vimentin and GFAP (Boehringer) to visualize glial cells.

Results

Cell Counts

Addition of D-β-hydroxybutyrate to the incubation resulted in an increase in the neuronal cell number per microisland from a mean of 30 to mean of 70 cells per microisland. Addition of 5 nM amyloid $β_{1-42}$ to the cultures reduced the cell numbers from 70 to 30 cells per microisland, confirming the previous observations of Hoshi et al, that amyloid $β_{1-42}$ is toxic to hippocampal neurons. Addition D-β-hydroxybutyrate to cultures containing amyloid $β_{1-42}$ increased the cell number from a mean of 30 to 70 cells per microisland. From these data we conclude that addition of substrate level quantities of D-β-hydroxybutyrate, to media whose major nutrients are glucose, pyruvate and L-glutamine, slows the rate of cell death in culture. We further conclude that D-β-hydroxybutyrate can decrease the increased rate of hippocampal cell death caused by the addition of amyloid $β_{1-42}$ in culture.

The number of dendritic outgrowths and the length of axons were both observed to have increased with presence of D-β-hydroxybutyrate, whether $β_{1-42}$ was present or not. This is indicative of nerve growth factor like behaviour.

Example 7
Preparation of (R,R,R)-4,8,12-trimethyl-1,5,9-trioxadodeca-2,6,10-trione: Triolide of (R)-3-hydroxybutyric Acid.

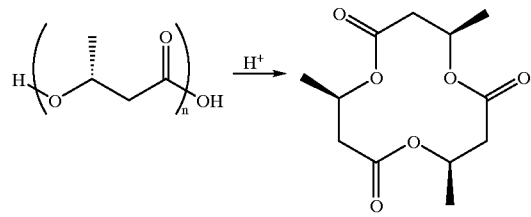

Synthesis was as described in Angew. Chem. Int. Ed. Engl. (1992), 31, 434. A mixture of poly[(R)-3-hydroxybutyric acid] (50 g) and toluene-4-sulphonic acid monohydrate (21.5 g, 0.113 mole) in toluene (840 ml) and 1,2-dichloroethane (210 ml) was stirred and heated to reflux for 20 hours. The water was removed by Dean-stark trap for 15 hours whereafter the brown solution was cooled to room temperature and washed first with a half saturated solution of sodium carbonate then with saturated sodium chloride, dried over magnesium sulphate and evacuated in vacuo. The brown semi-solid residue was distilled using a Kugelrohr apparatus to yield a white solid (18.1 g) at 120–130° C./0.15 mmHg. Above 130° C. a waxy solid began to distill—distillation being stopped at this point. The distilled material had mp 100–102° C. (literature mp 110–110.5° C.). Recrystallisation from hexane gave colourless crystals in yield 15.3 g. Mp=107–108° C.; $[\alpha]_D$ –35.1 (c=1.005, CHCl$_3$), (lit.=–33.9). $^1$H NMR (300 MHz, CDCl$_3$): δ=1.30 (d, 9H, CH$_3$); 2.4–2.6 (m,6H; CH$_2$); 5.31–5.39 (M,3H; HC—O). $^{13}$C NMR (CDCl$_3$) δ=20.86 (CH$_3$), 42.21 (CH$_2$), 68.92 (CH), 170.12 (CO). Elemental analysis: calculated for C$_{12}$H$_{18}$O$_6$: C, 55.81; H 7.02; Found: C, 55.67; H, 7.15.

Example 8

Oral Administration of Triolide of D-β-hydroxybutrate of Example 1 to Rats

The ability of orally administered tniolide to raise blood ketone levels was investigated as follows. The day before the experiment commenced, 12 Wistar rats weighing 316±10 g were placed in separate cages. They had no access to food for 15 hours prior to presentation with triolide containing compositions, but water was provided ad libitum.

On the morning of the experiment 0.64 g of triolide was mixed with 5 g Co-op brand Black Cherry yoghurt in separate feeding bowls for 9 of the rats. The remaining 3 rats were given 5 g of the yoghurt without the triolide as controls. The yoghurt containing bowls were placed in the cages and the rats timed while they ate. Two of the three control rats ate all the yoghurt and four of the six triolide yoghurt rats ate approximately half the provided amount. The remaining six rats slept.

Control rats (n=2) were killed at 60 and 180 minutes after ingestion of yoghurt while triolide fed rats were killed at 80, 140, 150 and 155 minutes. Blood samples were taken for assay of D-β-hydroxybutyrate. Brains were funnel frozen and later extracted in perchloric acid and extracts neutralised and assayed. Blood levels of (R)-3-hydroxybutrrate were measured using a NAD$^+$/EDTA assay of Anal. Biochem (1983) 131, p478–482. 1.0 ml of a solution made up from 2-amino-2-methyl-1-propanol (100 mM pH 9.9, 0.094 g/10 ml), NAD$^+$(30 mM, 0.199 g/10 ml) and EDTA (4 mM, 0.015 g/10 ml) was added to each of a number of cuvettes and 4µl sample or D-β-hydroxybutyrate control.

The two control rats ate 5.2±0.1 g yoghurt and their plasma (R)-3-hydroxybutyrate concentrations were about 0.45 mM at 60 minutes and 180 minutes. The four triolide fed rats ate 0.39±0.03 g of the triolide and 2.6±0.2 g of yoghurt. Their plasma D-β-hydroxybutyrate concentrations were 0.8 mM after 80 minutes and 1.1 mM for the group sacrificed at about 150 minutes. All rats displayed no ill effects from ingestion of triolide.

The test rats thus showed increase in plasma D-β-hydroxybutyrate over at least 3 hours with no ill effects. It should be noted that two other rats fed approximately 1.5 g triolide each in 'Hob-Nob' biscuit showed no ill effects after two weeks.

For all examples given above, it should be noted that the increased levels of (R)-3-hydroxybutyrate will also be mirrored in acetoacetate levels, not measured here, as there is a rapid establishment of equilibrium between the two in vivo such that acetoacetate levels will be between 40 and 100% of the (R)-3-hydroxybutyrate levels.

References

1. Cheung, J. Y., C. Conover, D. M. Regen, C. F. Whitfield, H. E. Morgan. Effect of insulin on kinetics of sugar transport in heart muscle. Am J Physiol 1978; 234: E70–E78.
2. Simpson, I. A., S. W. Cushman. Hormonal regulation of mammalian glucose transport. Annu Rev Biochem 1986; 55: 1059–1089.
3. Larner, J., J. C. Lawrence, R. J. Walkenbach, P. J. Roach, R. J. Hazen, L. C. Huang. Insulin control of glycogen synthesis. Adv Cyclic Nucleotide Res 1978; 9: 425–439).
4. Denton, R. M., P. J. Randle, B. J. Bridges, R. H. Cooper, A. L. Kerbey, H. T. Pask, D. L. Severson, D. Stansbie, S. Whitehouse. Regulation of mammalian pyruvate dehydrogenase. Mol Cell Biochem 1975; 9: 27–53).
5. Mukherjee, C., R. L. Jungas. Activation of pyruvate dehydrogenase in adipose tissue by insulin. Evidence for an effect of insulin on pyruvate dehydrogenase phosphate phosphatase. Biochem J 1975; 148: 229–235.
6. Randle, P. J., R. M. Denton, H. T. Pask, D. L. Severson. Calcium ions and the regulation of pyruvate dehydrogenase. Biochem Soc Symp 1974; 75–88.
7. Sodi-Pallares, D., M. R. Testelli, B. L. Fishleder, A. Bisteni, G. A. Medrano, C. Friedland, A. D. Micheli. Effects of an intravenous infusion of potassium-glucose-insulin solution on the electrographic signs of myocardial infarction. Am J Cardiol 1962; 9: 166–181.
8. Rackley, C. E., R. O. Russell, Jr., W. J. Rogers, J. A. Mantle, H. G. McDaniel, S. E. Papapietro. Clinical experience with glucose-insulin-potassium therapy in acute myocardial infarction. Am Heart J 1981; 102: 1038–1049.
9. Muller, J. E., S. Mochizuki, J. K. Koster, Jr., J. J. Collins, Jr., L. H. Cohn, S. R. Neely. Insulin therapy for depressed myocardial contractility after prolonged ischemia. Am J Cardiol 1978;41: 1215–1221.
10. Oliver, M. F., L. H. Opie. Effects of glucose and fatty acids on myocardial ischaemia and arrhythmias. Lancet 1994; 343: 155–158.
11. Taegtmeyer, H. The use of hypertonic glucose, insulin, and potassium (GIK) in myocardial preservation. J Appl Cardiol 1991; 6: 255–259.
12. McDaniel, H. G., S. E. Papapietro, W. J. Rogers, J. A. Mantle, L. R. Smith, R. O. Russell, Jr., C. E. Rackley. Glucose-lnsulin-potassium induced alterations in individual plasma free fatty acids in patients with acute myocardial infarction. Am Heart J 1981; 102: 10–15.
13. Cross, H. R., K. Clarke, L. H. Opie, G. K. Radda. Is lactate-induced myocardial ischaemic injury mediated by decreased pH or increased intracellular lactate? J Mol Cell Cardiol 1995; 27:1369–1381.
14. Cahill, G. F. Jr. Starvation in man. N Engl J Med 1970; 282: 668–675.
15. Sato, K., Y. Kashiwaya, C. A. Keon, N. Tsuchiya, M. T. King, G. K. Radda, B. Chance, K. Clarke, R. L. Veech. Insulin, ketone bodies, and mitochondrial energy transduction. FASEB J 1995; 9: 651–658.
16. Kashiwaya, Y., K. Sato, N. Tsuchiya, S. Thomas, D. A. Fell, R. L. Veech, J. V. Passonneau. Control of glucose utilization in workina perfused rat heart. J Biol Chem 1994; 269: 25502–25514.
17. Clarke, K., Y. Kashiwaya, M. T. King, D. Gates, C. A. Keon, H. R. Cross, G. K. Radda, R. L. Veech. The β/αpeak height ratio of ATP: a measure of free [Mg$^{2+}$] using $^{31}$P NMR. J Biol Chem 1996; 271: 21142–21150.
18. Veloso, D., R. W. Guynn, M. Oskarsson, R. L. Veech. The concentrations of free and bound magnesium in rat tissues. Relative constancy of free Mg$^{2+}$ concentrations. J Biol Chem 1973; 248: 4811–4819.
19. Chance, B., J. S. J. Leigh, J. Kent, K. McCully, S. Nioka, B. J. Clark, J. M. Maris, T. Graham. Multiple controls of oxidative metabolism in living tissues as studied by phosphorus magnetic resonance. Proc Natl Acad Sci USA 1986; 83: 9458–9462.

20. Veech, R. L., J. W. R. Lawson, N. W. Cornell, H. A. Krebs. Cytosolic phosphorylation potential. J Biol Chem 1979; 254: 6538–6547.
21. Passonneau, J. V., J. P. Schwartz, D. A. Rottenberg. The partial purification and properties of pig brain glycogen synthase. J Biol Chem 1975; 250: 2287–2292.
22. Michaelis, L., M. L. Menten. Die Kinetik der Invertinwirkung. Biochem Z 1913; 49: 333–369.
23. Haldane, J. B. S., Enzymes. London: Longmans, Green and Co. 1930: 74–92.
24. Kacser, H., J. A. Burns. The control of flux. Symp Soc Ecp Biol 1973; 27: 65–104.
25. Purich, D. L., H. J. Fromm, F. B. Rudolph. The hexokinases: kinetic, physical, and regulatory properties. Adv Enzymol Relat Areas Mol Biol 1973; 39: 249–326.
26. Casazza, J. P., R. L. Veech. The interdependence of glycolytic and pentose cycle intermediates in ad libitum fed rats. J Biol Chem 1986; 261: 690–698.
27. Randle, P. J. Metabolic fuel selection: general integration at the whole-body level. Proc Nutr Soc 1995; 54: 317–327.
28. Williamson, J. R., H. A. Krebs. Acetoacetate as fuel of respiration in the perfused rat heart. Biochem J 1961; 80: 540–547.
29. Taegtmeyer, H., R. Hems, H. A. Krebs. Utilization of energy-providing substrates in the isolated working rat heart. Biochem J 1980; 186: 701–711.
30. Halestrap, A. P., R. M. Denton. The specificity and metabolic implications of the inhibition of pyruvate transport in isolated mitochondria and intact tissue preparations by α-Cyano-4-hydroxycinnamate and related compounds. Biochem J 1975; 148: 97–106.
31. Williamson, D. H., P. Lund, H. A. Krebs. The redox state of free nicotinamide-adenine dinucleotide in the cytoplasm and mitochondria of rat liver. Biochem J 1967; 103: 514–527.
32. Krebs, H. A., R. L. Veech. The energy and metabolic control in mitochondria. Adriatica Editrice: Bari, 1969: 329–382.
33. Ozawa, K., H. Aoyama, K. Yasuda, Y. Shimahara, T. Nakatani, J. Tanaka, M. Yamamoto, Y. Kamiyama, T. Tobe. Metabolic abnormalities associated with postoperative organ failure. A redox theory. Arch Surg 1983; 118: 1245–1251.
34. Tanaka, A., T. Kitai, A. Tokuka, T. Inomoto, H. J. Kim, K. Tanaka, Y. Yamaoka, K. Ozawa. Increased span of oxido-reduction states between pyridine nucleotide and cytochrome c oxidase in the regenerating rabbit liver as measured by arterial ketone body ratio and near-infrared spectroscopy. Res Exp Med (Berl) 1993; 193: 353–359.
35. Veech, R. L., D. N. Gates, C. W. Crutchfield, W. L. Gitomer, Y. Kashiwaya, M. T. King, R. Wondergem. Metabolic hyperpolarization of liver by ethanol: The importance of $Mg^{2+}$ and $H^+$ in determining impermeant intracellular anionic charge and energy of metabolic reactions. Alcohol Clin Exp Res 1994; 18: 1040–1056.
36. Lawson, J. W. R., R. L. Veech. Effects of pH and free $Mg^{2+}$ on the Keq of the creatine kinase reaction and other phosphate hydrolyses and phosphate transfer reactions. J Biol Chem 1979; 254: 6528–6537.
37. Hochachka, P. W., C. M. Clark, J. E. Holden, C. Stanley, K. Ugurbil, R. S. Menon. $^{31}P$ magnetic resonance spectroscopy of the Sherpa heart: a phosphocreatine/adenosine triphosphate signature of metabolic defense against hypobaric hypoxia. Proc Natl Acad Sci USA 1996; 93: 1215–1220.
38. Klingenberg, M. Metabolite transport in mitochondria: an example for intracellular membrane function. Essays Biochem 1970; 6: 119–159.
39. Coty, W. A., P. L. Pedersen. Phosphate transport in rat liver mitochondria, Kinetics and energy requirements. J Biol Chem 1974; 249: 2593–2598.
40. Masuda, T., G. P. Dobson, R. L. Veech. The Gibbs-Donnan near-equilibrium system of heart. J Biol Chem 1990; 265: 20321–20334.
41. Romani, A., A. Scarpa. cAMP control of $Mg^{2+}$ homeostasis in heart and liver cells. Magnes Res 1992; 5: 131–137.
42. Veech, R. L., Y. Kashiwaya, M. T. King. The resting potential of cells are measures of electrical work not of ionic currents. Int Physiol Behav Sci 1995; 30: 283–306.
43. Denton, R. M., J. G. McCormack, P. J. Midgley, G. A. Rutter. Hormonal regulation of fluxes through pyruvate dehydrogenase and the citric acid cycle in mammalian tissues. Biochem Soc Symp 1987; 54: 127–143.
44. Saladin, R, P. De Vos, M. Guerre-Millo, A. Leturque, J. Girard, B. Staels, J. Auwerx. Transient increase in obese gene expression after food intake or insulin administration. Nature 1995; 377: 527–529.
45. Apstein, C. S., F. N. Gravino, C. C. Haudenschild. Determinants of a protective effect of glucose and insulin on the ischemic myocardium. Effects on contractile function, diastolic compliance, metabolism, and ultrastructure during ischemia and reperfusion. Circ Res 1983; 52: 515–526.
46. Mantle, J. A., W. J. Rogers, L. R. Smith, H. G. McDaniel, S. E. Papapietro, R. O. Russell Jr., C. E. Rackley. Clinical effects of glucose-insulin-potassium on left ventricular function in acute myocardial infarction: results from a randomized clinical trial. Am Heart J 1981; 102: 313–324.
47. Owen, O. E., A. P. Morcran, H. G. Kemp, J. M. Sullivan, M. G. Herrera, G. F. Cahill, Jr. Brain metabolism during fasting. J Clin Invest 1967; 46: 1589–1595.
48. Veech, R. L. The toxic impact of parenteral solutions on the metabolism of cells: a hypothesis for physiological parenteral therapy. Am J Clin Nutr 1986; 44: 519–551.
49. Chan, L., J. Slater, J. Hasbargen, D. N. Herndon, R. L. Veech, S. Wolf. Neurocardiac toxicity of racemic D,L-lactate fluids. Integr Physiol Behav Sci 1994; 29: 383–394.
50. ISIS4. A randomised factorial trial assessing early oral captopril, oral mononitrate, and intravenous magnesium sulphate in 58,050 patients with suspected acute myocardial infarction. Lancet 1995; 345: 669–685.
51. Seelig, M. S., R. J. Elin. Is there a place for magnesium in the treatment of acute myocardial infarction? Am Heart J 1996; 132: 471–477.
52. McLean, R M. Magnesium and its therapeutic uses: a review. Am J Med 1994; 96: 63–76
53. Ma, J., A. R. Folsom, S. L. Melnick, J. H. Eckfeldt, A. R. Sharrett, A. A. Nabulsi, R. G. Hutchinson, P. A. Metcalf Associations of scrum and dietary magnesium with cardiovascular disease, hypertension. diabetes, insulin, and carotid arterial wall thickness: the ARIC study. Atherosclerosis Risk in Communities Study. J Clin Epidemiol 1995; 48: 927–940.
54. Ozono, R., T. Oshima, H. Matsuura, Y. Higashi, T. Ishida, M. Watanabe, M. Yoshimura, H. Hiraga, N. Ono, G. Kajiyama. Systemic magnesium deficiency disclosed by magnesium loading test in patients with essential hypertension. Hypertens Res 1995; 18: 39–42.
55. Rasmussen, H. S., P. McNair, L. Goransson, S. Balslov, O. G. Larsen, P. Aurup. Magnesium deficiency in patients with ischemic heart disease with and without acute myocardial infarction uncovered by an intravenous loading test. Arch Intern Med 1988; 148: 329–332.

56. Amari, A., N. C. Grace, W. W. Fisher. Achieving and maintaining compliance with the ketogenic diet. J Appl Behav Anal 28: 341–342, 1995.
57. Bartus, R. T., R. L. Dean, 3d, B. Beer, A. S. Lippa. The cholinergic hypothesis of geriatric memory dysfunction. Science 217: 408–414, 1982.
58. Beylot, M., D. Chassard, C. Chambrier, M. Guiraud, M. Odeon, B. Beaufrere, P. Bouletreau. Metabolic effects of a D-beta-hydroxybutyrate infusion in septic patients: inhibition of lipolysis and glucose production but not leucine oxidation. Crit Care Med 22: 1091–1098, 1994.
59. Birkhahn, R. H., J. R. Border. Intravenous feeding of the rate with short chain fatty acid esters. II Monoacetoacetin. Am J Clin Nutr 31: 436–441, 1978
60. Brashear, A., G. A. Cook. A spectrophotometric, enzymatic assay for D-3-hydroxybutyrate that is not dependent on hydrazine. Anal Biochem 131: 478–482, 1983.
61. Brion, J. P. The neurobiology of Alzheimer's disease. Acta Clin Belg 51: 80–90 1996.
62. Cahill, G. F., Jr. Starvation in man. N Engl J Med 282: 668–675, 1970.
63. Cahill, G. F., Jr., T. T. Aoki. Alternative Fuel Utilization in Brain. In: Cerebral metabolism and neural function, edited by J. V. Passonneau, R. A. Hawkins, W. D. Lust, and F. A. Welsh, Baltimore, Williams & Wilkins, 1980, p. 234–242.
64. Chan, L., J. Slater, J. Hasbargen, D. N. Herndon, R. L. Veech, S. Wolf Neurocardiac toxicity of racemic D, L-lactate fluids, Integr Physiol Behav Sci 29: 383–394, 1994.
65. Chartier-Harlin, M. C., F. Crawford, H. Houlden, A. Warren, D. Hughes, L. Fidani, A. Goate, M. Rossor, P. Roques, J. Hardy Early-onset Alzheimer's disease caused by mutations at codon 717 of the beta-amyloid precursor protein gene. Nature 353: 844–846, 1991.
66. Corder, E. H., A. M. Saunders, W. J. Strittmatter, D. E. Schmechel, P. C. Gaskell, G. W. Small, A. D. Roses, J. L. Haines, M. A. Pericak-Vance. Gene dose of apolipoprotein E type 4 allele and the risk of Alzheimer's disease in late onset families (see comments), Science 261: 921–923, 1993.
67. Desrochers, S., P. Dubreuil, J. Brunet, M. Jette, F. David, B. R. Landau, H. Btunengraber. Metabolism of (R,S)-1, 3-butanediol acetoacetate esters, potential parenteral and enteral nutrients in conscious pigs. Am J Physiol 286: E660-7, 1995.
68. Desrochers, S., K. Quinze, H. Dugas, P. Dubreuil, C. Bomont, F. David, K. C. Agarwal, A. Kumar, M. V. Soloviev, L. Powers, B. R. Landau, H. Brunengraber. (R.S.) 1,3 butandiol acetoacetate esters, potential alternatives to lipid emulsions for total parenteral nutrition. J Nutr Biochem 6: 109–116, 1995.
69. Feany, M. B., D. W. Dickson. Neurodegenerative disorders with extensive tau pathology: a comparative study and review. Ann Neurol 40:139–148, 1996.
70. Fox, N. C., E. K. Warrington, P. A. Freeborough, P. Hartikainen, A. M. Kennedy, J. M. Stevens, M. N. Rossor. Presymptomatic hippocampal atrophy in Alzheimer's disease. A longitudinal MRI study. Brain 119: 2001–2007, 1996
71. Freeman, J. M., E. P. G. Vining. Intractable epilepsy. Epilepsia 33: 1132–1136, 1992.
72. Goate, A., M. C. Chartier-Harlin, M. Mullan, J. Brown, F. Crawford, L. Fidani, A. Giuffra, A. Haynes, N. Irving, L. James. Segregation of a missense mutation in the amyloid precursor protein gene with familial Alzheimer's disease (see comments). Nature 349: 704–706, 1991.
73. Graham, D. I., S. M. Gentleman, J. A. Nicoll, M. C. Royston, J. E. McKenzie, G. W. Roberts, W. S. Griffin. Altered beta-APP metabolism after head injury and its relationship to the aetiology of Alzheimer's disease. Acta Neurochir Suppl (Wien). 66: 96–102, 1996.
74. Gumbiner, B., J. A. Wendel, M. P. McDermott. Effects of diet composition and ketosis on glycemia during very-low-energy-diet therapy in obese patients with non-insulin-dependent diabetes mellitus. Am J Clin Nutr 63: 110–115, 1996.
75. Halestrap, A. P. The mitochondrial pyruvate carrier. Kinetics and specificity for substrates and inhibitors. Biochem J 148: 85–96, 1975.
76. Hawkins, R. A., J. F. Biebuyck. Regional brain utilization of ketone bodies. In: Cerebral metabolism and neural function, edited by J. V. Passonneau, R. A. Hawkins, W. D. Lust, and F. A. Welsh. Baltimore: Williams & Wilkins, 1980, p. 255–263.
77. Hoshi, M., A. Takashima, M. Murayama, K. Yasutake, N. Yoshida, K. Ishiguro, T. Hoshino, K. Imahori. Nontoxic amyloid ,β peptide $_{1\text{-}42}$ suppresses acetylcholine synthesis. J Biol Chem 272: 2038–2041, 1997.
78. Hoshi, M., A. Takashima, K. Noguchi, M. Murayama, M. Sato, S. Kondo, Y. Saitoh, K. Ishiguro, T. Hoshino, K. Imahori. Regulation of mitochondrial pyruvate dehydrogenase activity by tau protein kinase I/glycogen synthase kinase 3beta in brain. Proc Natl Acad Sci U.S.A. 93: 2719–2723, 1996
79. Hutton, M., F. Busfield, M. Wragg, R. Crook, J. Perez-Tur, R. F. Clark, G. Prihar, C. Talbot, H. Phillips, K. Wright, M. Baker, C. Lendon, K. Duff, A. Martinez, H. Houlden, A. Nichols, E. Karran, G. Roberts, P. Roques, M. Rossor, J. C. Venter, M. D. Adams, R. T. Cline, C. A. Phillips, A. Goate. Complete analysis of the presenilin 1 gene in early onset Alzheimer's disease. Neuroreport. 7: 801–805, 1996.
80. Kashiwaya, Y., K. Sato, N. Tsuchiya, S. Thomas, D. A. Fell, R. L. Veech, J. V. Passonneau. Control of glucose utilization in working perfused rat heart. J Biol Chem 269: 25502–25514, 1994.
81. Kies, C., R. B. Tobin, H. M. Fox, M. A. Mehlman. Utilization of 1,3-butanediol and nonspecific nitrogen in human adults. J. Nutr. 103: 1155–1163, 1973
82. Kripke, S. A., A. D. Fox, J. M. Berman, J. DePaula, R. H. Birkhahn, J. L. Rombeau, R. G. Settle. Inhibition of TPN-associated intestinal mucosal atrophy with monoacetoacetin. J Surg Res 44: 436–444. 1988.
83. Langfort, J., W. Pilis, R. Zarzeczny, K. Nazar, H. Kaciuba-Uscilko. Effect of low-carbohydrate-ketogenic diet on metabolic and hormonal responses to graded exercise in men. J Physiol Pharmacol 47: 361–371, 1996.
84. Lawson, J. W. R., R. W. Guynn, N. W. Cornell, R. L. Veech. Gluconeogenesis, Its regulation in mammalian species. In: edited by R. W. Hanson and M. A. Mehlman, John Wiley & Sons: New York, 1976, p. 481–514.
85. Maiz, A., L. L. Moldawer, B. R. Bistrian, R. H. Birkhahn, C. L. Long, G. L. Blackburn. Monoacetoacetin and protein metabolism during parenteral nutrition in burned rates. Biochem J 226: 43–50, 1985.
86. Masuda, T., G. P. Dobson, R. L. Veech. The Gibbs-Donnan near-equilibrium system of heart. J. Biol. Chem 265: 20321–20334, 1990.
87. Mehlman, M. A., R. L. Veech. Redox and phosphorylation states and metabolite concentrations in frozen clamped livers of rats fed diets containing 1,3-butanediol and DL-carnitine. J Nutr 102: 45–51, 1972.
88. Nebeling, L. C., E. Lerner. Implementing a ketogenic diet based on medium-chain triglyceride oil in pediatric patents with cancer. J Am Diet Assoc 95: 693–697, 1995.

89. Nebeling, L. C., F. Miraldi, S. B. Shurin, E. Lerner. Effects of a ketogenic diet on tumor metabolism and nutritional status in pediatric oncology patents: two case reports. J Am Coll Nutr 14: 202–208, 1995.
90. Oster-Granite, M. L., D. L. McPhie, J. Greenan, R. L. Neve. Age-dependent neuronal and synaptic degeneration in mice transgenic for the C terminus of the amyloid precursor protein. J Neurosci 16: 6732–6741, 1996.
91. Owen, O. E., A. P. Morgan, H. G. Kemp, J. M. Sullivan, M. G. Herrera, G. F. Cahill, Jr. Brain metabolism during fasting. J Clin Invest 46: 1589–1595, 1967.
92. Paradis, E., H. Douillard, M. Koutroumanis, C. Goodyer, A. LeBlanc. Amyloid beta peptide of Alzheimer's disease downregulates Bcl-2 and upregulates bax expression in human neurons. J Neurosci 16:7533–7539, 1996.
93. Rhie, H. G., D. Dennis. Role of fadR and atoC(Con) mutations in poly(3-hydroxy-butyrate-co-3-hydroxyvalerate) synthesis in recombinant pha-*Escherichia coli*. Appl Environ Microbiol 61: 2487–2492, 1995.
94. Rossor, M. N. Catastrophe, chaos and Alzheimer's disease. The F E Williams Lecture. J R Coll Physicians Lond 29: 412–418, 1995.
95. Sato, K., Y. Kashiwaya, C. A. Keon, N. Tsuchiya, M. T. King, G. K. Radda, B. Chance, K. Clarke, R. L. Veech. Insulin, Ketone bodies, and mitochondrial energy transduction, FASEB J 9: 651–658, 1995.
96. Selkoe, D. J. Alzheimer's disease: genotypes, phenotypes, and treatments. Science 275: 630–631, 1997.
97. Sheng, J. G., K. Ito, R. D. Skinner, R. E. Mak, C. R. Rovnaghi, L. J. Van Eldik, W. S. Griffin. In vivo and in vitro evidence supporting a role for the inflammatory cytokine interleukin-1 as a driving force in Alzheimer pathogenesis. Neurobiol Aging 17: 761–766, 1996.
98. Strittmatter, W. J., A. D. Roses. Apolipoprotein E and Alzheimer disease. Proc Natl Acad Sci U.S.A. 92: 4725–4727, 1995.
99. Taegtmeyer, H., R. Hems, H. A. Krebs. Utilization of energy-providing substrates in the isolated working rat heart. Biochem J 186: 701–711, 1980.
100. Talbot, C., H. Houlden, H. Craddock, R. Crook, M. Hutton, C. Lendon, G. Prihar, J. C. Morris, J. Hardy, A. Goate. Polymorphism in AACT gene may lower age of onset of Alzheimer's disease. Neuroreport. 7: 534–536, 1996.
101. Tobin, R. B., M. A. Mehlman, C. Kies, H. M. Fox, J. S. Soeldner. Nutritional and metabolic studies in humans with 1,3-butanediol. Fed Proc 34: 2171–2176, 1975.
102. Valentin, H. F., D. Dennis. Metabolic pathway for poly(3-hydroxybutyrate-co-3-hydroxyvalerate) formation in Nocardia corallina: inactivation of mutB by chromosomal integration of a kanamycin resistance gene. Appl Environ Microbio 62: 372–379, 1996.
103. Veech, R. L. The toxic impact of parenteral solutions on the metabolism of cells: a hypothesis for physiological parenteral therapy. Am J Clin Nutr 44: 519–551, 1986.
104. Veech, R. L. The untoward effects of the anions of dialysis fluids. Kidney Int 34: 587–597, 1988.
105. Veech, R. L., W. L. Gitomer. The medical and metabolic consequences of administration of sodium acetate. Adv Enzyme Regul 27: 313–343, 1988.
106. Veech, R. L., R. W. Guynn, D. Veloso. The time-course of the effects of ethanol on the redox and phosphorylation states of rat liver. Biochem J 127: 387–397, 1972.
107. Veech, R. L., R. L. Harris, M. A. Mehlman. Brain metabolite concentrations and redox states in rats fed diets containing 1,3-butanediol and ethanol. Toxicol Appl Pharmacol 29: 196–203, 1974.
108. Wang, J. Z., I. Grundke-Iqbal, K. Iqbal. Restoration of biological activity of alzheimer abnormally phosphorylated tau by dephosphoryulation with protein phosphatase-2A, -2B and -1. Brain Res Mol Brain Res 38: 200–208, 1996.
109. Wilder, R. M. Effect of ketonuria on the course of epilepsy. Mayo Clin Bull 2: 307-ff, 1921.
110. Williamson, D. H., P. Lund, H. A. Krebs. The redox state of free nicotinamide-adenine dinucleotide in the cytoplasm and mitochondria of rat liver. Biochem J 103: 514–527, 1967.
111. Williamson, D. H., J. Mellanby, H. A. Krebs. Biochem J 82: 90–96, 1962.
112. Wing, R. R., H. A. Vazquez, C. M. Ryan. Cognitive effects of ketogenic weight-reducing diets. Int J Obes Relat Metab Disord 19: 811–816, 1995.
113. Zhang, H., V. Obias, K. Gonyer, D. Dennis. Production of polyhydroxylakanoates in sucrose-utilizing recombinant *Escherichia coli* and Klebsiella strains. Appl environ microbiol 60: 1198–1205, 1994.

What is claimed is:

1. A method of treating a patient for a neuro-degenerative disorder selected from the group consisting of those involving inability to metabolise glucose inhibition of pyruvate dehydrogenase memory loss in aging, neurotoxic peptides or proteins, and genetic abnormality comprising administering to that patient a therapeutically effective amount of one or more of D-β-hydroxybutyric acid, acetoacetate, or a metabolic precursor or physiologically acceptable salt of D-β-3-hydroxybutyric acid or acetoacetate, such as to elevate the patient's blood level of ketone bodies, defined as the sum total of D-β-hydroxybutyric acid and acetoacetate, to a therapeutic level effective to treat the disorder wherein when a metabolic precursor is administered it is not hydroxybutyryl carnitine.

2. A method of treating a patient in order to treat a neuro-degenerative disorder selected from the group consisting of those involving inability to metabolise glucose, inhibition of pyruvate dehydrogenase, memory loss in aging, neurotoxic peptides or proteins, and genetic abnormality comprising administering to that patient a therapeutically effective amount of at least one of D-β-hydroxybutyric acid, acetoacetate, or a metabolic precursor or physiologically acceptable salt of D-β-hydroxybutyric acid or acetoacetate, such as to elevate the patient's blood level of ketone bodies, defined as the sum total of D-β-hydroxybutyric acid and acetoacetate, to a therapeutic level effective to treat the disorder wherein the patient's blood level is elevated to from 0.3 mM to 20 mM.

3. A method of treating a CNS cell, peripheral nerve cell, or otherwise insulin insensitive cell in need of therapy for a condition selected from the group consisting of one or more of neuro-degeneration in which the cell is subject to inhibition of pyruvate dehydrogenase, neurotoxic effects of pathogenic peptides, proteins and genetic abnormality, GABA preventable seizure, or insufficient ability to metabolise glucose, comprising administering to that cell one or more compounds selected from the group consisting of D-β-hydroxybutyric acid, acetoacetate, compounds which are oligomers of D-β-hydroxybutyric acid, acetoacetyl esters of D-β-hydroxybutyric acid and acetoacetyl esters of oligomers of D-β-hydroxybutyric acid, and physiologically acceptable salts thereof.

4. A method of treating a patient for a condition selected from the group consisting of epilepsy, diabetes or an insulin resistant state comprising administering to that patient a therapeutically effective amount of one or more compounds selected from the group consisting of D-β-hydroxybutyric acid, acetoacetate and metabolic precursors of D-β-hydroxybutyric acid or acetoacetate which comprise moieties selected from the group consisting of R-1,3-butandiol, acetoacetyl and D-β-hydroxybutyryl moieties and physiologically acceptable salts and esters thereof.

5. A method as claimed in claim 1, claim 2, claim 3 or claim 4 wherein on administration of the compound to an unfasted patient in need of such therapy, the blood level of ketone bodies, defined as the sum total of D-β-hydroxybutyric acid and acetoacetate, is raised to between 0.3 and 20 mM.

6. A method as claimed in claim 1, claim 2, claim 3 or claim 4 wherein the neurodegenerative disorder is selected from those involving neurotoxic protein plaques.

7. A method as claimed in claim 1, claim 2, claim 3 or claim 4 wherein the metabolic precursor is selected from the group consisting of Free Fatty Acids and compounds comprising 1,3-butandiol, acetoacetyl or D-β-hydroxybutyryl moieties.

8. A method as claimed in claim 7 wherein the metabolic precursor is a polymer or oligomer of D-β-hydroxybutyrate.

9. A method as claimed in claim 8 wherein the metabolic precursor is an acetoacetyl ester.

10. A method as claimed in claim 8 wherein metabolic precursor is selected from the group consisting of compounds of general formulae:

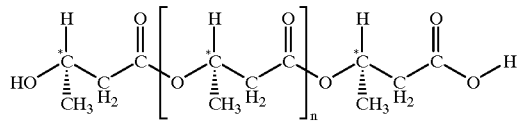

and

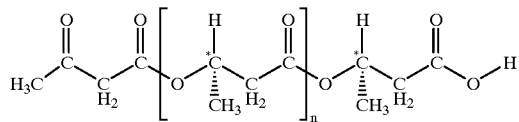

or physiologicial acceptable salts or esters thereof wherein in each case n is selected such that the polymer or oligomer is readily metabolised on administration to a human or animal body to provide elevated ketone body levels in blood.

11. A method as claimed in claim 10 wherein n is an integer of 0 to 1,000.

12. A method as claimed in claim 10 wherein n is an integer of from 1 to 5.

13. A method as claimed in claim 1, wherein the level of ketone bodies produced in the blood is in the ratio 1:1 to 20:1 of D-β-hydroxybutyrate to acetoacetate.

14. A method as claimed in claim 8 wherein the oligomer is a cyclic oligomer of formula

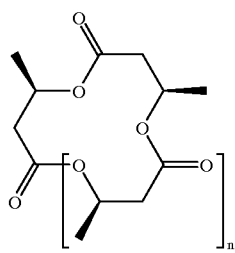

where n is an integer of 1 or more or a complex thereof with one or more cations or a salt thereof.

15. A method as claimed in claim 14 wherein the one or more cations are selected from the group consisting of sodium, potassium, magnesium and calcium.

16. A method as claimed in claim 14 wherein n is an integer from 1 to to 20.

17. A method as claimed in claim 14 wherein the oligomer is (R, R, R)-4, 8, 12-trimethyl-1, 5, 9-trioxadodeca-2, 6, 10-trione.

18. A composition comprising a compound selected from those claimed in claim 14 and poly D-β-hydroxybutyrate together with a physiologically acceptable carrier, in sterile and pyrogen free form.

19. A method as claimed in claim 1 or claim 2 wherein the patient is in need of therapy for brain cell neurodegeneration due to Alzheimer's disease or Parkinson's disease.

* * * * *

UNITED STATES PATENT AND TRADEMARK OFFICE
CERTIFICATE OF CORRECTION

PATENT NO.        : 6,323,237 B1                                           Page 1 of 1
APPLICATION NO.   : 09/397100
DATED             : November 27, 2001
INVENTOR(S)       : Richard L. Veech It is certified that error appears in the above-identified patent and that said Letters Patent is hereby corrected as shown below:

Column 1, lines 3-10, please cancel the two paragraphs and replace by the following single paragraph:

"This is a continuation in part of PCT application No. PCT/US98/05072, filed Mar. 17, 1998, the entire content of which is hereby incorporated by reference in this application, which application No. PCT/US98/05072 claims the benefit of U.S. Provisional Application No. 60/040,858, filed Mar. 17, 1997, the entire content of which is hereby incorporated by reference in this application."

Signed and Sealed this

Third Day of February, 2009

JOHN DOLL
*Acting Director of the United States Patent and Trademark Office*